United States Patent
Snow

(10) Patent No.: US 10,925,561 B2
(45) Date of Patent: Feb. 23, 2021

(54) PORTABLE DIGITAL RADIOGRAPHY APPARATUS COMPRISING A FRAME INCLUDING A BASE, A DIGITAL RADIOGRAPHY PANEL, AND A COMPUTER

(71) Applicant: KONICA MINOLTA HEALTHCARE AMERICAS, INC., Wayne, NJ (US)

(72) Inventor: Terry Snow, Oak Harbor, WA (US)

(73) Assignee: KONICA MINOLTA HEALTHCARE AMERICAS, INC., Wayne, NJ (US)

( * ) Notice: Subject to any disclaimer, the term of this patent is extended or adjusted under 35 U.S.C. 154(b) by 20 days.

(21) Appl. No.: 16/193,763

(22) Filed: Nov. 16, 2018

(65) Prior Publication Data

US 2019/0167216 A1 Jun. 6, 2019

Related U.S. Application Data

(60) Provisional application No. 62/638,363, filed on Mar. 5, 2018, provisional application No. 62/587,900, filed on Nov. 17, 2017.

(51) Int. Cl.
*A61B 6/00* (2006.01)

(52) U.S. Cl.
CPC .............. *A61B 6/4405* (2013.01); *A61B 6/42* (2013.01); *A61B 6/4208* (2013.01); *A61B 6/4283* (2013.01); *A61B 6/44* (2013.01); *A61B 6/4411* (2013.01); *A61B 6/4452* (2013.01); *A61B 6/46* (2013.01); *A61B 6/461* (2013.01); *A61B 6/462* (2013.01); *A61B 6/467* (2013.01); *A61B 6/508* (2013.01); *A61B 6/56* (2013.01)

(58) Field of Classification Search
CPC ....... A61B 6/42; A61B 6/4208; A61B 6/4283; A61B 6/44; A61B 6/4405; A61B 6/4411; A61B 6/4452; A61B 6/46; A61B 6/461; A61B 6/462; A61B 6/467; A61B 6/508; A61B 6/56
USPC .............. 378/62, 98.8, 189, 198; 250/370.09
See application file for complete search history.

(56) References Cited

U.S. PATENT DOCUMENTS

| | | | | |
|---|---|---|---|---|
| 5,608,774 A | * | 3/1997 | Polichar | G01N 23/04 378/102 |
| 7,247,859 B2 | * | 7/2007 | Murphy | A61B 6/00 250/370.09 |
| 7,343,001 B2 | * | 3/2008 | Abu Tabanjeh | A61B 6/00 378/116 |
| 7,438,470 B2 | * | 10/2008 | Koren | A61B 6/00 378/198 |

(Continued)

*Primary Examiner* — Allen C. Ho
(74) *Attorney, Agent, or Firm* — Lucas & Mercanti, LLP

(57) ABSTRACT

A portable digital radiography apparatus includes a frame including a base, a radiography panel configured to be accommodated on the frame, a computer configured to be accommodated on the frame, and a charging system disposed in the base, the charging system being connectable to the radiography panel and the computer and configured to charge both the radiography panel and the computer when the radiography panel and the computer are accommodated on the frame. The frame, the radiography panel, the computer, and the charging system are transportable as an integral unit when the radiography panel and the computer are accommodated on the frame.

25 Claims, 19 Drawing Sheets

(56) References Cited

U.S. PATENT DOCUMENTS

| | | | | |
|---|---|---|---|---|
| 7,573,034 B2* | 8/2009 | Heath | ................... | G03B 42/02 |
| | | | | 250/361 R |
| 8,021,045 B2* | 9/2011 | Foos | ................... | A61B 6/4405 |
| | | | | 378/198 |
| 8,622,614 B2* | 1/2014 | Carmichael | ......... | A61B 6/4266 |
| | | | | 378/198 |
| 8,755,492 B2* | 6/2014 | Lee | .......................... | H05G 1/02 |
| | | | | 378/115 |
| 8,781,073 B2* | 7/2014 | Kim | ......................... | A61B 6/46 |
| | | | | 378/98 |
| 8,950,938 B2* | 2/2015 | Liu | ..................... | A61B 6/5211 |
| | | | | 378/207 |
| 8,961,011 B2* | 2/2015 | Lalena | ................. | A61B 6/4405 |
| | | | | 378/197 |
| 9,125,611 B2* | 9/2015 | Eaves | ................. | A61B 6/4405 |
| 9,149,247 B2* | 10/2015 | Lee | ..................... | A61B 6/4452 |
| 9,168,016 B2* | 10/2015 | Ohta | ......................... | G01T 1/24 |
| 9,402,592 B2* | 8/2016 | Garcia | ................ | A61B 6/5294 |
| 9,405,183 B2* | 8/2016 | Ando | ................. | A61B 6/4266 |
| 9,521,983 B2* | 12/2016 | Jang | ..................... | A61B 6/4429 |
| 9,757,080 B2* | 9/2017 | Lee | ..................... | A61B 6/4452 |
| 9,855,017 B2* | 1/2018 | Wojcik | ................ | A61B 6/4233 |
| 9,931,089 B2* | 4/2018 | Nariyuki | ............ | A61B 6/4411 |
| 9,949,702 B2* | 4/2018 | Nam | ..................... | G21K 1/025 |
| 9,952,339 B2* | 4/2018 | Koh | ......................... | G01T 1/17 |
| 9,973,988 B2* | 5/2018 | Ando | ................... | H04W 36/20 |
| 9,980,358 B2* | 5/2018 | Kim | ....................... | H05G 1/54 |
| 9,980,696 B2* | 5/2018 | Oda | ..................... | A61B 6/465 |
| 9,992,853 B2* | 6/2018 | Kim | ....................... | H05G 1/56 |
| 9,993,221 B2* | 6/2018 | Kim | ..................... | A61B 6/547 |
| 10,022,105 B2* | 7/2018 | Kudo | ................... | A61B 6/563 |
| 10,028,710 B2* | 7/2018 | Kim | ....................... | A61B 6/467 |
| 10,033,955 B2* | 7/2018 | Kimura | ............... | A61B 6/4233 |
| 10,034,643 B2* | 7/2018 | Kim | ................... | A61B 6/5241 |
| 10,034,649 B2* | 7/2018 | Kim | ..................... | A61B 6/544 |
| 10,045,751 B2* | 8/2018 | Okusu | ................... | A61B 6/563 |
| 10,051,718 B2* | 8/2018 | Kim | ..................... | H02J 7/0031 |
| 10,058,297 B2* | 8/2018 | Park | ..................... | A61B 6/4494 |
| 10,098,609 B2* | 10/2018 | Kim | ....................... | A61B 6/587 |
| 10,111,642 B2* | 10/2018 | Deinlein | ................ | A61B 6/547 |
| 10,136,866 B2* | 11/2018 | Onobori | ................ | A61B 6/4458 |
| 10,143,428 B2* | 12/2018 | Eun | ....................... | A61B 6/461 |
| 10,172,578 B2* | 1/2019 | Lee | .......................... | A61B 6/52 |
| 10,188,365 B2* | 1/2019 | Lee | ......................... | A61B 6/40 |
| 10,219,766 B2* | 3/2019 | Park | ....................... | A61B 6/465 |
| 10,258,300 B2* | 4/2019 | Onobori | ................. | A61B 6/00 |
| 10,258,307 B2* | 4/2019 | Park | ..................... | A61B 6/4452 |
| 10,285,664 B2* | 5/2019 | Song | ..................... | A61B 6/4417 |
| 10,295,975 B2* | 5/2019 | Kim | ..................... | A61B 6/4411 |
| 10,321,883 B2* | 6/2019 | Kim | ....................... | G01R 31/50 |
| 10,327,729 B2* | 6/2019 | Hayashi | ................. | A61B 6/566 |
| 10,390,779 B2* | 8/2019 | Kim | ......................... | A61B 6/54 |
| 10,398,400 B2* | 9/2019 | Kim | ....................... | A61B 6/545 |
| 10,433,809 B2* | 10/2019 | Park | ....................... | H04W 84/20 |
| 10,440,805 B2* | 10/2019 | Imamura | ................ | H05G 1/58 |
| 10,456,100 B2* | 10/2019 | Ninomiya | ........... | A61B 6/4452 |
| 10,462,887 B2* | 10/2019 | Kuranisi | ................. | H05G 1/06 |
| 10,478,146 B2* | 11/2019 | Matsuura | ............. | A61B 6/4283 |
| 10,506,695 B2* | 12/2019 | Boehm | ................... | H05G 1/32 |
| 10,517,561 B2* | 12/2019 | Lin | ..................... | A61B 6/547 |
| 10,531,850 B2* | 1/2020 | Tkaczyk | ............... | A61B 6/0487 |
| 10,575,803 B2* | 3/2020 | Hattori | ................... | A61B 6/467 |
| 10,603,000 B2* | 3/2020 | Hattori | ................ | A61B 6/4494 |
| 10,610,171 B2* | 4/2020 | Imamura | ............... | A61B 6/465 |
| 10,617,304 B2* | 4/2020 | Ohta | ...................... | A61B 8/56 |
| 10,631,817 B2* | 4/2020 | Kim | ....................... | G01R 31/3842 |
| 10,631,818 B2* | 4/2020 | Vogelsang | ........... | A61B 6/5264 |
| 10,646,177 B2* | 5/2020 | Kim | ....................... | A61B 6/56 |
| 10,660,584 B2* | 5/2020 | Tajima | ................... | A61B 6/461 |
| 10,667,670 B2* | 6/2020 | Ohta | ................... | A61B 8/0891 |
| 10,667,772 B2* | 6/2020 | Mikami | ................ | A61B 90/50 |
| 10,729,394 B1* | 8/2020 | Foos | ..................... | A61B 6/587 |
| 10,765,388 B2* | 9/2020 | Nozawa | ................ | A61B 6/461 |
| 10,765,397 B2* | 9/2020 | Komasaka | ........... | A61B 6/4283 |
| 10,772,587 B2* | 9/2020 | Sanbuichi | ................ | A61B 6/40 |
| 10,779,779 B2* | 9/2020 | Hayakawa | ............. | A61B 6/06 |
| 10,786,215 B2* | 9/2020 | Nakamura | ............. | A61B 6/06 |
| 10,799,189 B2* | 10/2020 | Nye | ....................... | A61B 6/032 |

\* cited by examiner

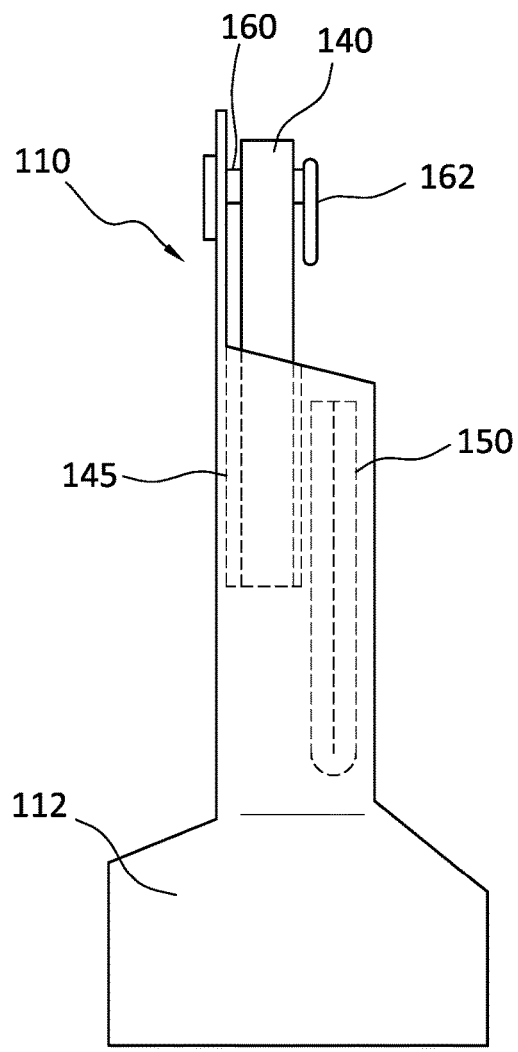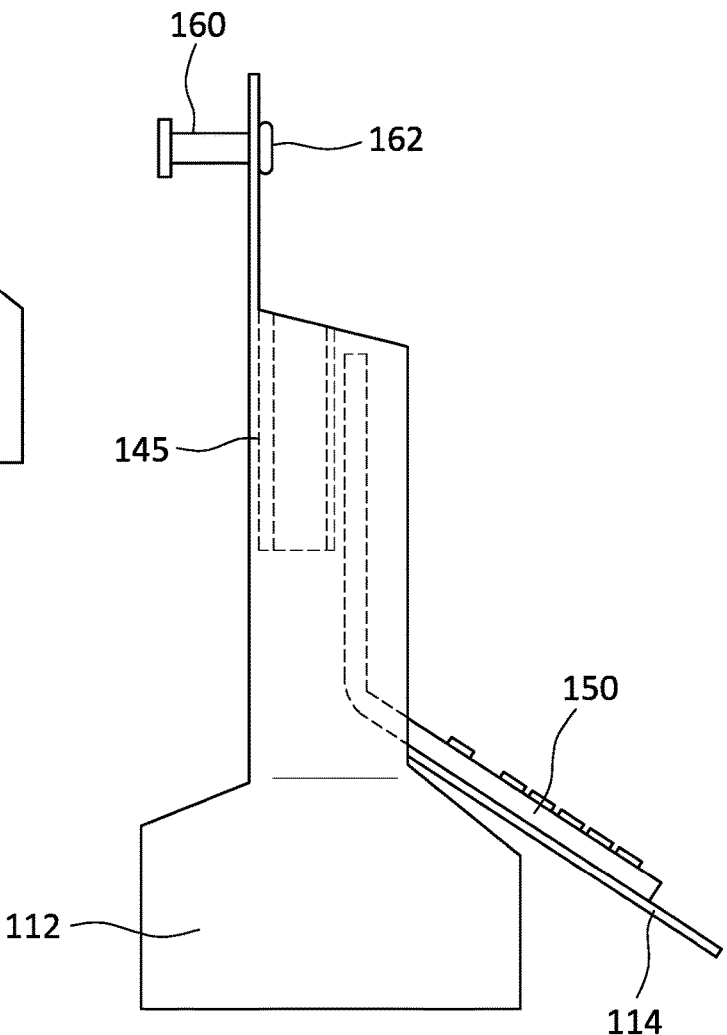
FIG. 7
FIG. 8

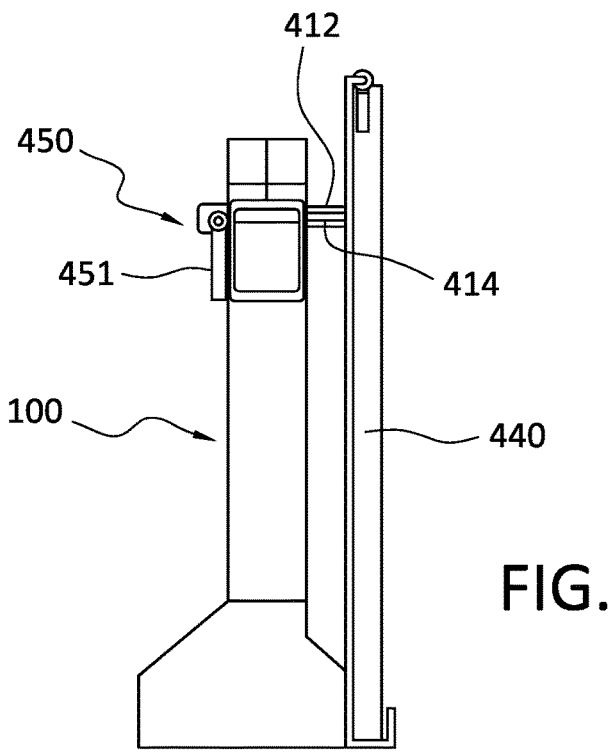
FIG. 19
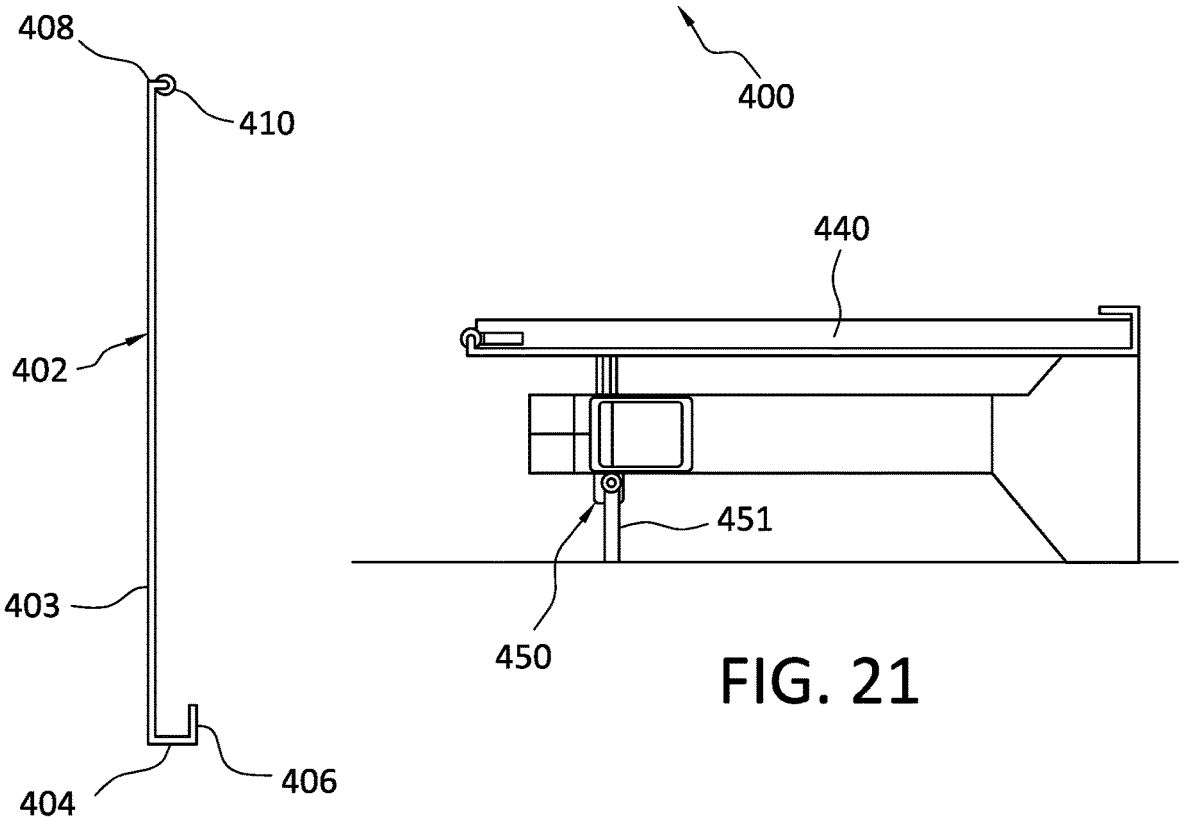
FIG. 20
FIG. 21

PORTABLE DIGITAL RADIOGRAPHY APPARATUS COMPRISING A FRAME INCLUDING A BASE, A DIGITAL RADIOGRAPHY PANEL, AND A COMPUTER

CROSS-REFERENCE TO RELATED APPLICATIONS

The present application claims priority to Provisional Application No. 62/587,900, filed Nov. 17, 2017 and Provisional Application No. 62/638,363, filed on Mar. 5, 2018, the entire contents of which are incorporated herein by reference.

BACKGROUND OF THE INVENTION

The present invention relates to a portable digital radiography apparatus for taking x-rays with a digital radiography panel or computed radiography panel.

In the field of portable digital radiography for veterinary purposes, the equipment is required to be transported to the animal to be imaged. The many different pieces of equipment required make this a cumbersome task.

Although some prior art systems include travel cases, it is still difficult to remove the equipment from the cases and repack the equipment after the imaging is completed.

Moreover, it is difficult to charge all of the individual pieces of equipment.

SUMMARY OF THE INVENTION

An object of the present invention is to provide a portable digital radiography apparatus that is easier to use than the prior art systems.

The object of the invention is met by a portable digital radiography apparatus including a frame having a base, a radiography panel, the frame being configured to accommodate the radiography panel, a computer (i.e., laptop or tablet), the frame configured to accommodate the computer, and a charging system connectable to the radiography panel and the computer and configured to charge both the radiography panel and the computer when the radiography panel and the computer are accommodated on the frame. The frame, the radiography panel, the computer, and the charging system are transportable as an integral unit when the radiography panel the computer are accommodated on the frame.

According to an embodiment of the invention, the radiography panel is mounted in a first holder, the first holder has a first holder handle, and the portable digital radiography apparatus is liftable by the first holder handle when the first holder is accommodated on the frame.

In a further embodiment, a second holder is provided with an enclosure in which the computer is mounted. The frame accommodates the second holder.

In a preferred embodiment, the frame includes side rails defining slots in which side walls of the first holder and the second holder are slidably received, whereby each of the first holder and the second holder is vertically receivable in the frame and vertically removable from the frame via the slots.

At least one locking lever is arranged on the rails that is movable from a locked position to an unlocked position. The at least one locking lever engages a recess in a side post of the first holder and a side post of the second holder when the at least one locking lever is in the locked position and allow removal of the first holder and the second holder from the frame when the at least one locking lever is in the unlocked position.

The portable digital radiography apparatus can be grasped and lifted by a user's hand. More specifically, the user can lift the apparatus by the first holder handle and/or the second holder handle when the first holder and/or the second holder are accommodated on the frame and the at least one locking lever is in the locked position. The total weight of the apparatus including the frame, the first holder, and the second holder is approximately 18 pounds, 10 ounces.

In a further embodiment, the base includes an electrical connection for forming an electrical connection elements for forming an electrical connection between the charging system and both the computer and the radiography panel, wherein both the computer and the radiography panel can be charged simultaneously through the base.

In a further embodiment, the radiography panel is mounted in a first holder, and the first holder is receivable in a slot or receptacle on the frame.

A panel power supply is arranged in the base for charging the radiography panel. The slot or receptacle includes a first set of contacts connected to the panel power supply, and the first holder includes a second set of contacts that coincide with the first set of contacts and provide an electrical connection between the radiography panel and the panel power supply when the first holder is received in the slot or the receptacle.

The frame includes an enclosure in which the computer is mounted and the enclosure has a hinged cover that opens to provide access to the computer. The computer in this embodiment is a laptop computer and the hinged cover supports the keyboard. The enclosure is removable from the frame.

A computer power supply for charging the computer is arranged in the base. The frame including a third set of contacts connected to the computer power supply, and the enclosure, or a holder in which the enclosure is mounted, includes a fourth set of contacts that coincide with the third set of contacts and provide an electrical connection between the computer and the computer power supply when the enclosure is mounted on the frame.

In a preferred embodiment, the apparatus includes a locking element capable of holding the radiography panel onto the frame in a locked position.

The radiography panel is mounted in a first holder, the frame has a frame handle, and the apparatus can be carried using the frame handle when the radiography panel is held onto the frame by the locking element.

The frame is pivotable relative to the base when the computer is a tablet computer so that a viewing angle can be adjusted.

The panel is configured to capture images while accommodated on the frame, whereby the frame acts as a stand for the panel.

The apparatus may additionally include a mounting connected to the frame for accommodating an additional radiography panel, the comprising a bracket that supports a bottom and a top of the additional radiography panel. In this embodiment the apparatus includes a support leg that is movable between a stowed position and a deployed position, the support leg supporting the apparatus of the portable digital radiography apparatus is laid on its side so that the additional radiography panel is facing upward and is parallel to the ground supporting the portable digital radiography apparatus The term laptop used in the specification and the claims includes laptop and notebook computers, and any other portable personal computer with a "clamshell" form. The term tablet used in the specification and the claims includes tablet computers and any other portable computers with a single flat package.

BRIEF DESCRIPTION OF THE DRAWINGS

In the drawings:

FIG. 7 is a side view of a portable digital radiography apparatus according to a second embodiment of the present invention;

FIG. 8 is a side view of the portable digital radiography apparatus of FIG. 7 with the digital radiography panel removed;

FIG. 19 is a side view of another embodiment of the present invention;

FIG. 20 is a side view of a bracket used in the embodiment of FIG. 19;

FIG. 21 is a side view of the embodiment of FIG. 19 supported in a horizontal position;

DETAILED DESCRIPTION OF THE PREFERRED EMBODIMENTS

Figures 1A, 2:
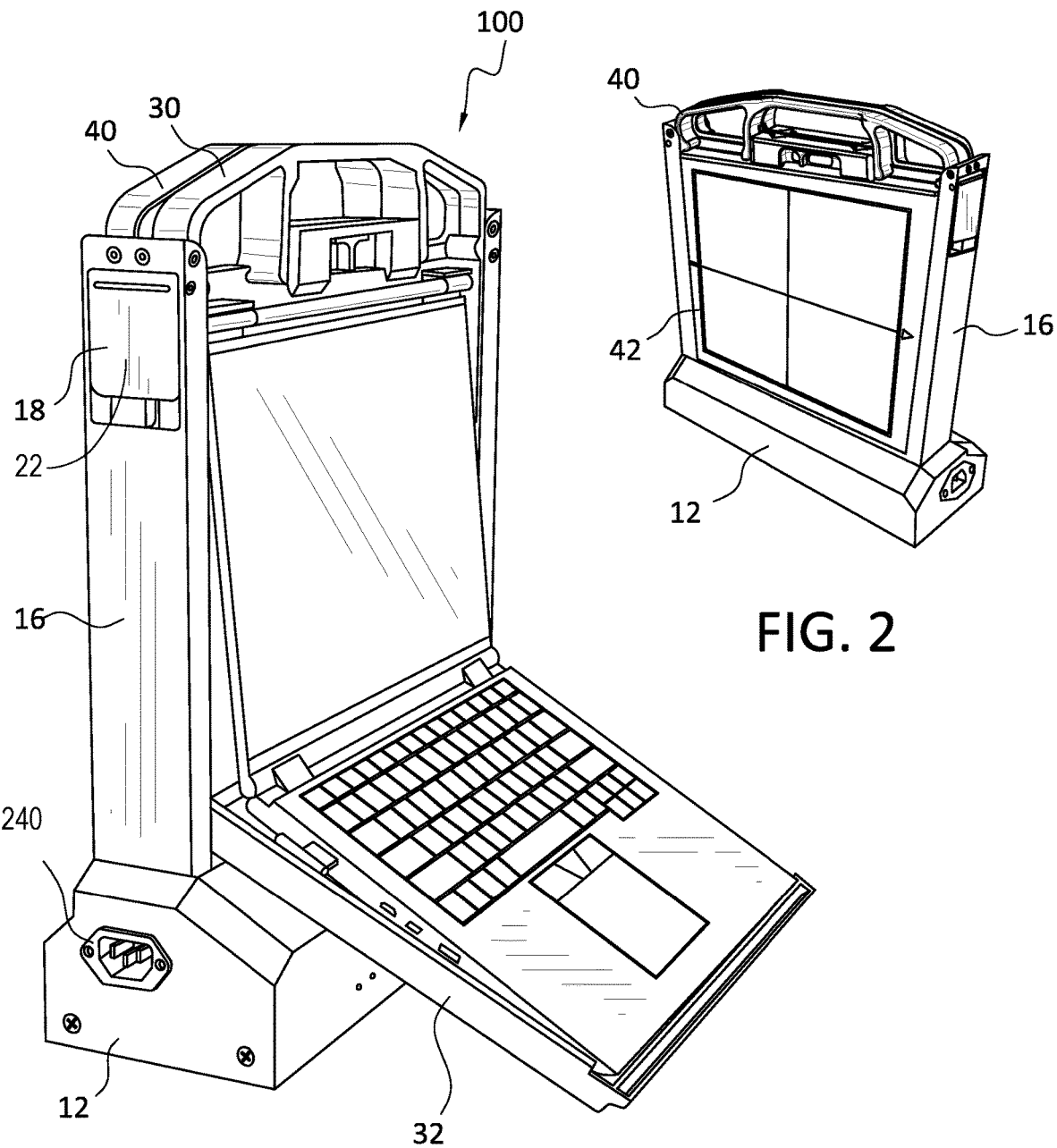
FIG. 1A is a perspective view of a front and a left side of a portable digital radiography apparatus according to a first embodiment of the present invention.
FIG. 2 is a perspective view of a rear and the left side of the portable digital radiography apparatus of FIG. 1A.

FIGS. 1A-3 show a portable digital radiography apparatus 100 having a base 12 and a frame 10 with side rails 16 and a handle 14. Bottom ends of the side rails 16 are connected to opposing sides of the base 12 and upper ends of the side rails 16 are connected to opposing sides of the handle 14. In some embodiments, the frame 10 may also extend into the base 12. The frame 10 is made of aluminum or plastic. However, any suitable material can be used.

Figure 3:
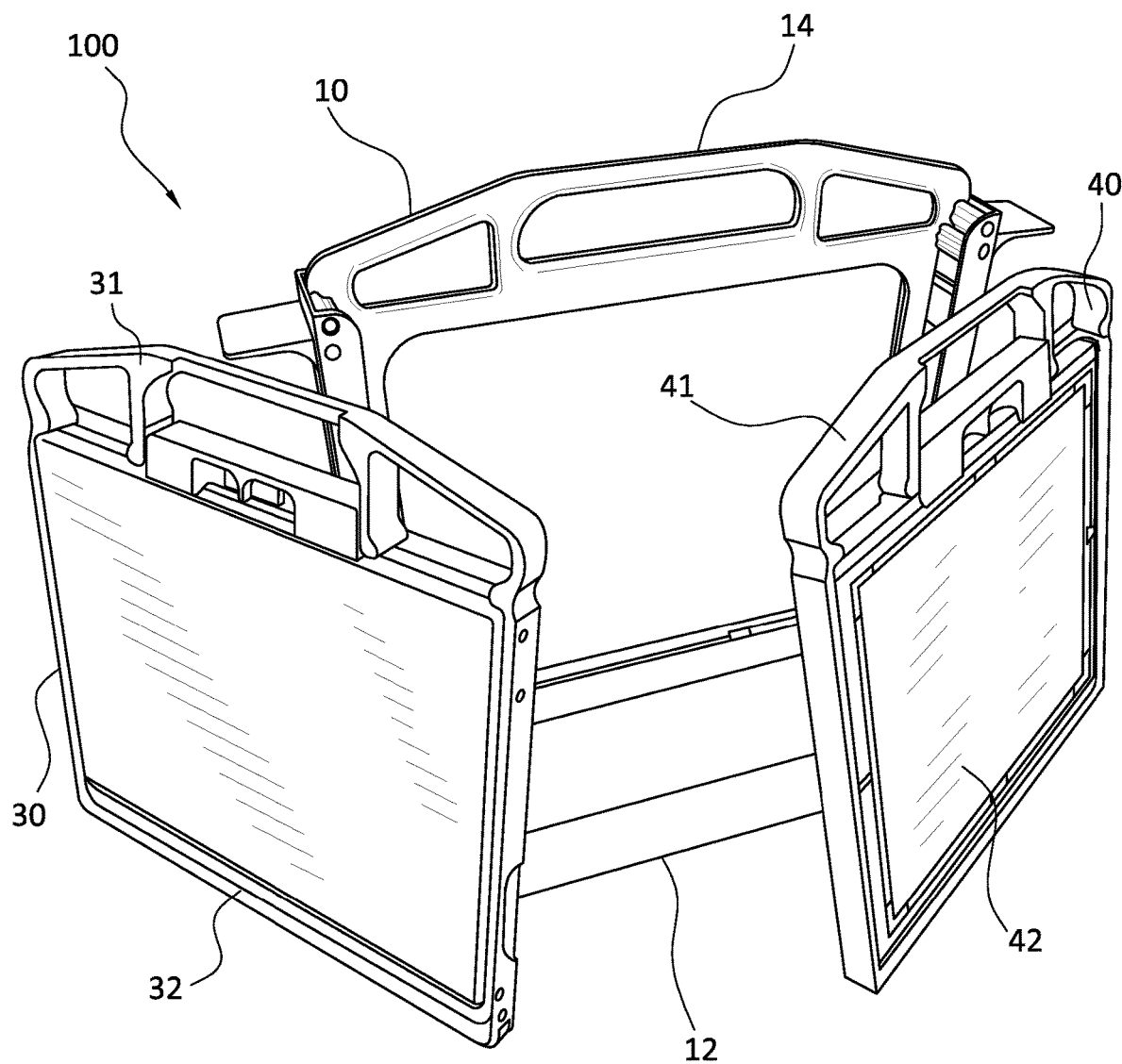
FIG. 3 is a perspective view of the portable digital radiography apparatus of FIG. 1A with the components in a separated state.
Figure 5:
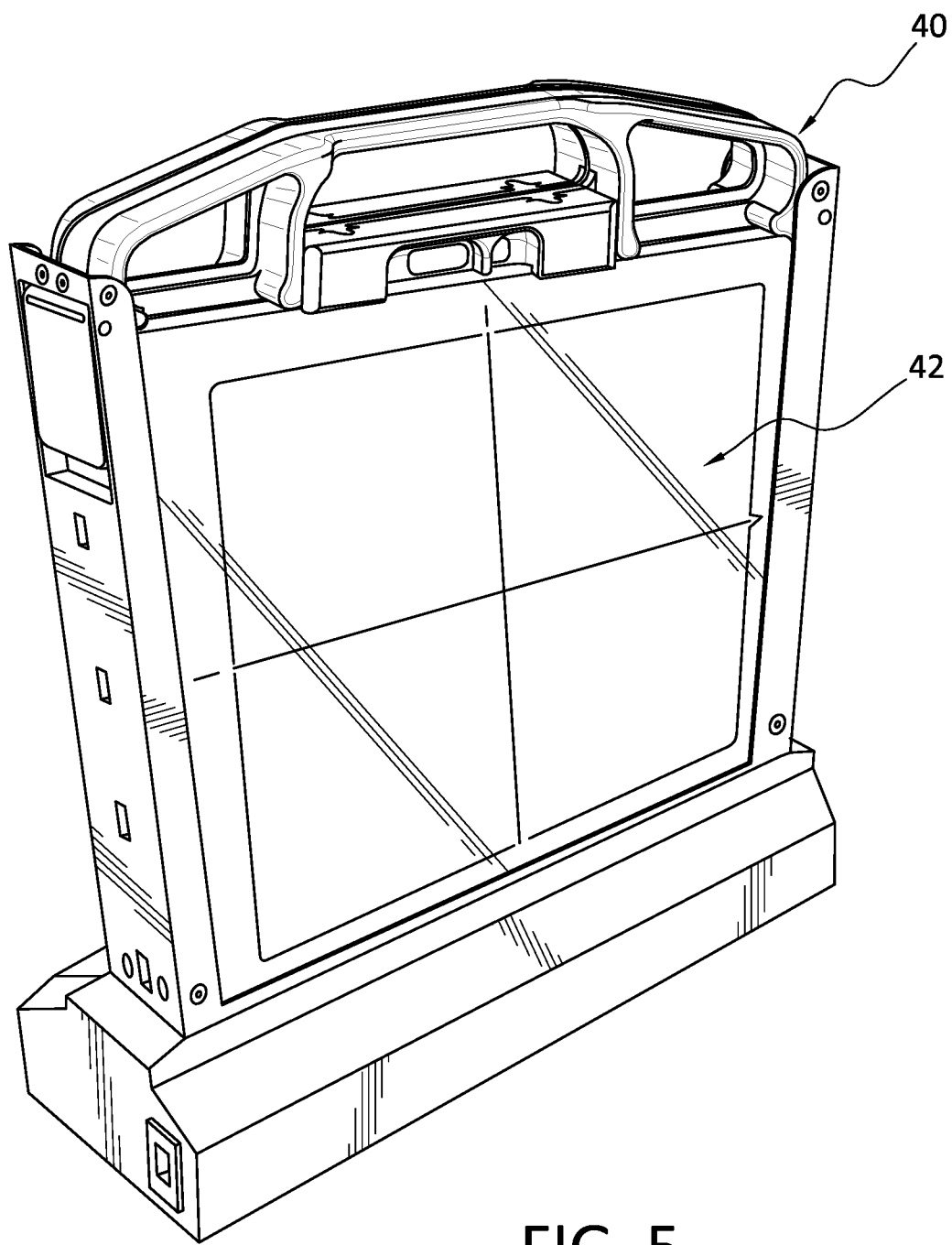
FIG. 5 is a front view of the first holder of the portable digital radiography apparatus of FIG. 1A.

FIGS. 3 and 5 show a first holder 40 that holds a digital radiography panel 42. In a preferred embodiment, the first holder 40 is a Protect-A-Grid™ encasement. However, any holder that meets the requirements will suffice. In a preferred embodiment the digital radiography panel 42 is a flat panel detector with a cesium iodide scintillator manufactured by Konica Minolta. However, the digital radiography panel 42 may be any type of digital radiography panel such as, for example, flat panel detector, CCD detectors, or phosphor plate detectors. Alternatively, the digital radiography panel 42 could be a computed radiography panel.

Figure 4:
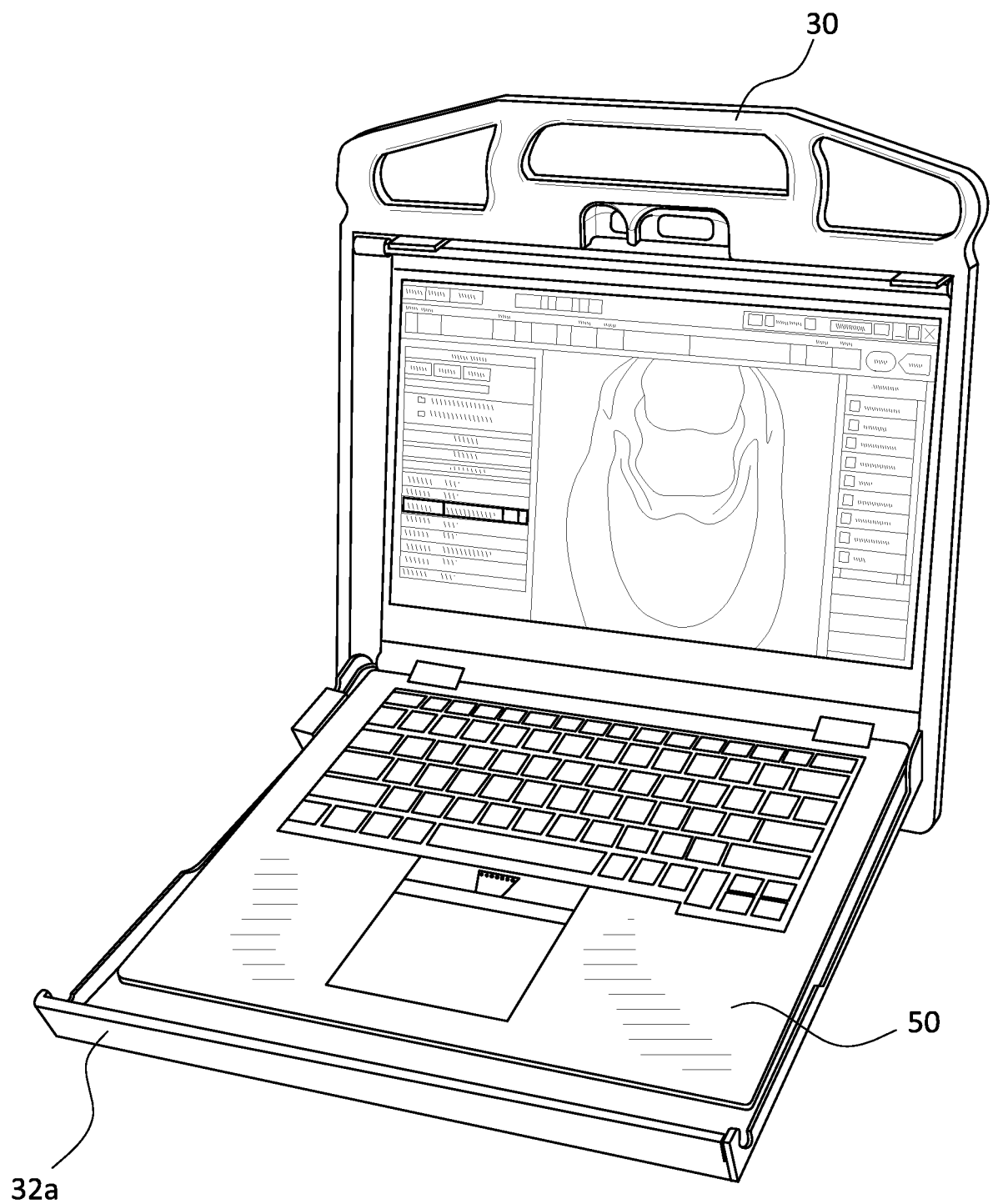
FIG. 4 is a front view of a second holder of the portable digital radiography apparatus of FIG. 1A in an open state.

FIGS. 3 and 4 show a second holder 30 that holds an enclosure 32, which is configured to hold a computer 50 (i.e., a laptop or tablet). The portable digital radiography apparatus 100 is configured to accommodate the second holder 30. A front wall 32a of the enclosure 32 is pivotally connected and provides a tray surface for the keyboard of the computer 50 in an open position. The computer 50 can be used while the second holder 30 is accommodated in the frame 10. Alternatively, the second holder 30 can be removed so that the computer 50 can also be used remotely from the frame 10. The second holder 30 has a handle portion 31 that coincides with the handle 14 of the frame 10 when the second holder 30 is received in the frame 10. Although the computer 50 is preferably a laptop or tablet, the computer 50 can be any other computing device known or hereafter developed that can perform the functions as described below.

The frame 10 is configured to accommodate the first holder 40 on a side of the frame 10 opposite from the second holder 30, whereby the frame 10, the second holder 30, and the first holder 40 are transportable as a single unit.

The handle portion 41 of the first holder 40 also coincides with the handle 14 of the frame 10. Accordingly, when the first holder 40 and the second holder 30 are received or accommodated in the frame 10, the handle portion 31, the handle portion 41, and the handle 14 are aligned to form an integrated handle. In further embodiments shown in FIGS. 17 and 18, the frame 10 does not have a handle and the portable digital radiography apparatus 100 is lifted solely by the handle portions 31, 41 of the first holder 40 and the second holder 30, as described in more detail below.

The second holder 30 is similar to the first holder 40, but is custom made for the enclosure 32.

Figure 3A:
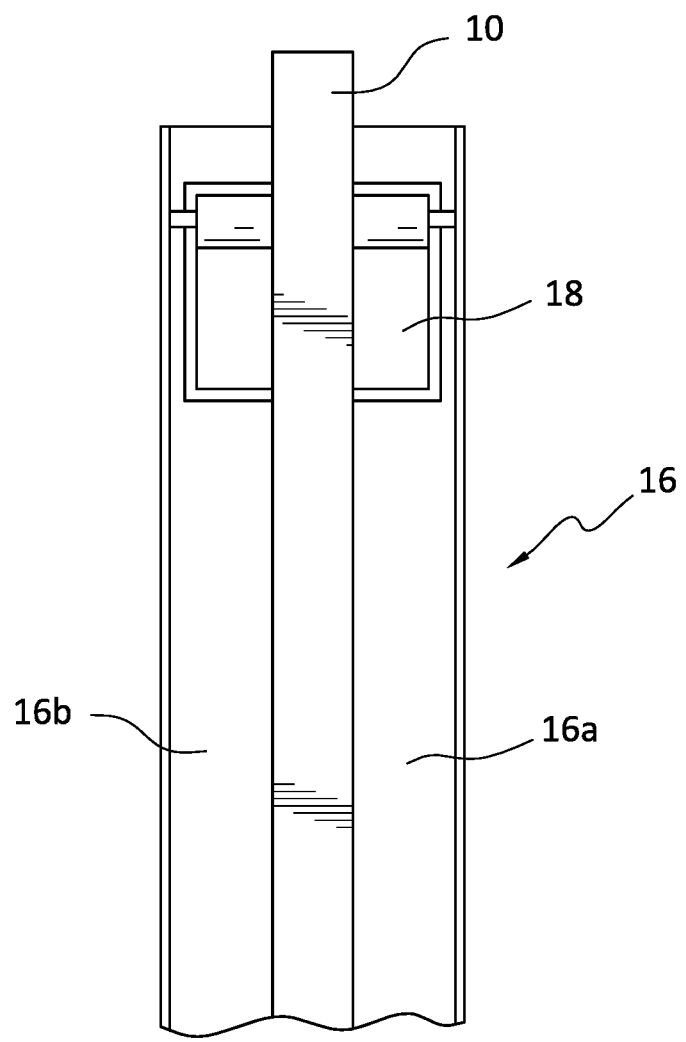
FIG. 3A is a side view of an inside of a side rail of the apparatus of FIG. 1A.

Each of the side rails 16 of the frame 10 defines slots 16a, 16b on a front side a rear side of the frame 10 in which the first holder 40 and the second holder 30 are slidably received (see FIG. 3A). Thus, each of the first holder 40 and the second holder 30 are vertically received in the frame 10 and vertically removable from the frame 10 via the slots 16a, 16b.

Figure 6A:
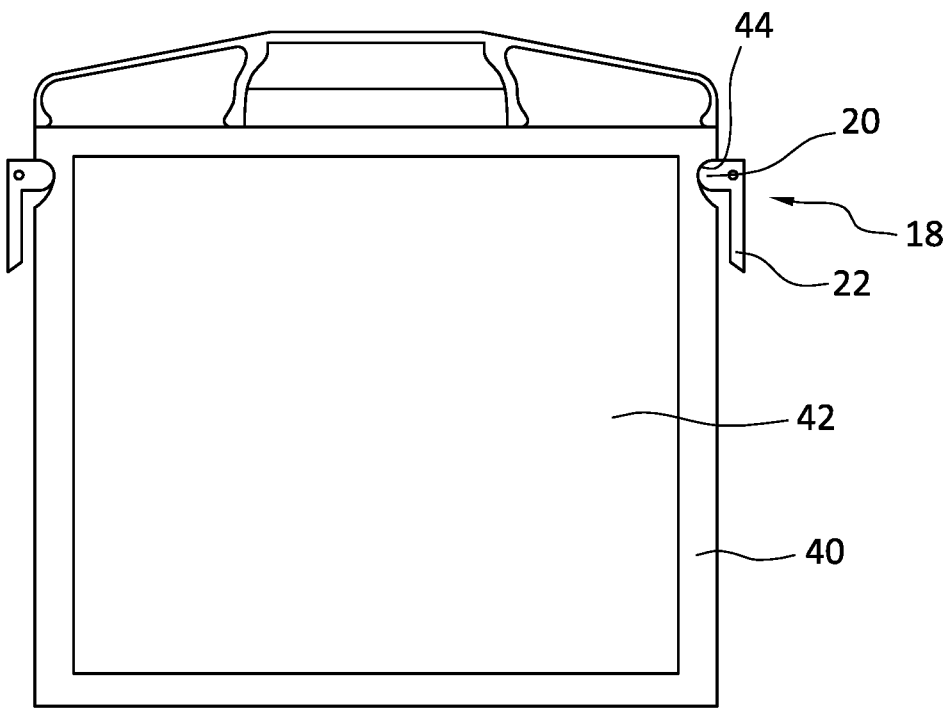
FIG. 6A is a front view of the first holder of the portable digital radiography apparatus of FIG. 1A and a position of locking tabs in a locked state.
Figure 6B:
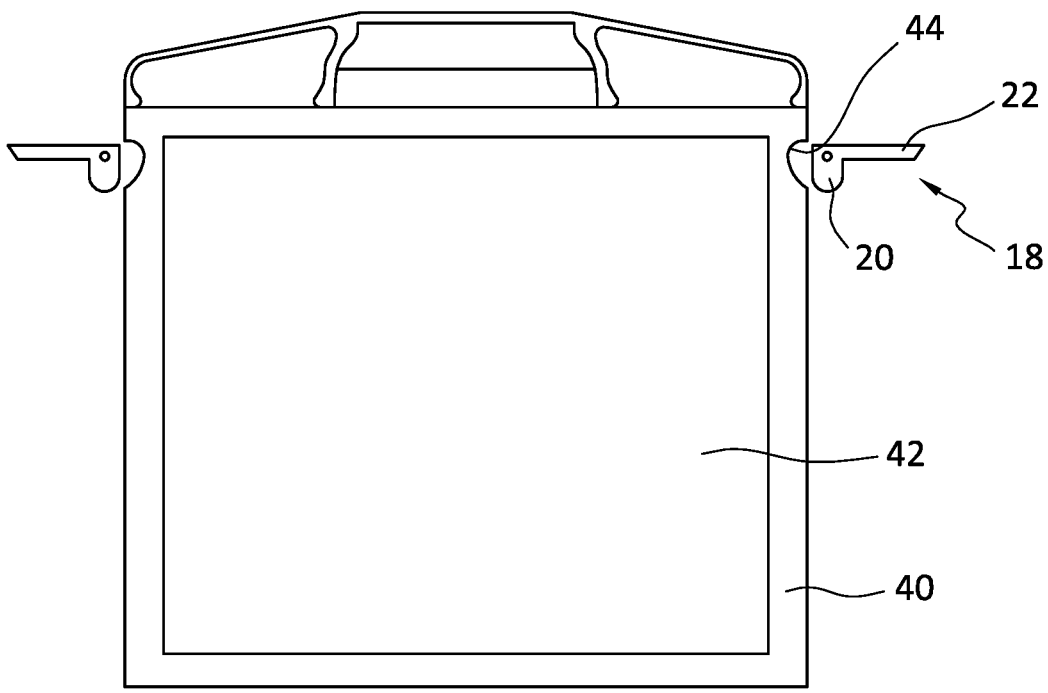
FIG. 6B is a front view of the first holder of FIG. 6A with a position of the locking tabs in a released state.

FIGS. 1, 3, and 3A also show locking levers 18 arranged on the side rails 16 that are movable from a locked position to an unlocked position. Each of the locking levers 18 includes a projection 20 and a lever 22. FIGS. 6A and 6B show the relative positions of the locking levers 18 relative to the first holder 40. In the locked position, the projections 20 of the locking levers 18 engage recesses 44 in the side walls or side posts of the first holder 40 (FIG. 6A) and the levers 22 extend in the direction of side rail 16, i.e., a vertical direction (FIG. 1). In the unlocked or released position, projections 20 of the locking levers 18 are disengaged from the recesses 44 and allow removal of the first holder 40 (FIG. 6B) and the levers 22 extend horizontally (FIG. 3). The locking levers 18 operate similarly with respect to the second holder 30.

Figure 10:
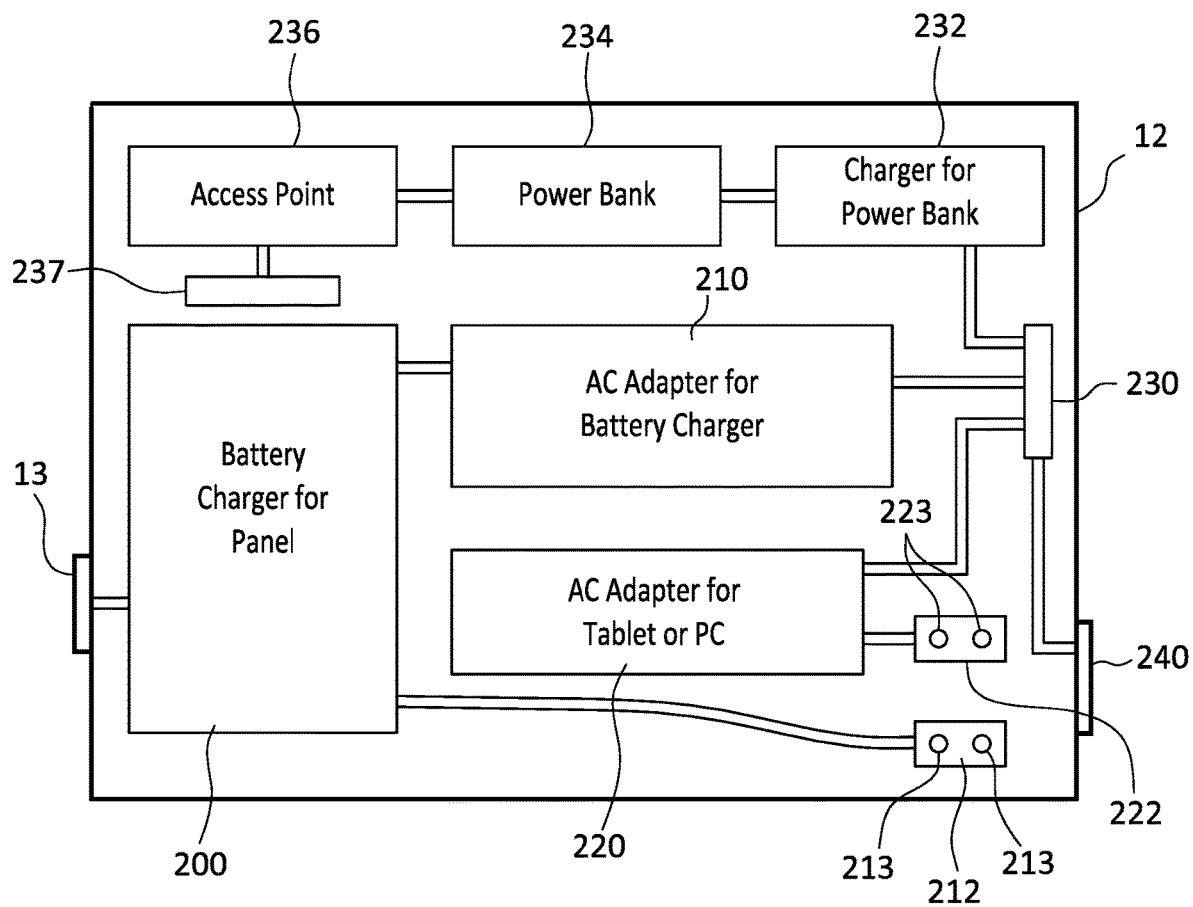
FIG. 10 is a schematic diagram of the components in a base of the portable digital radiography apparatus of FIG. 1A.
Figure 11A:
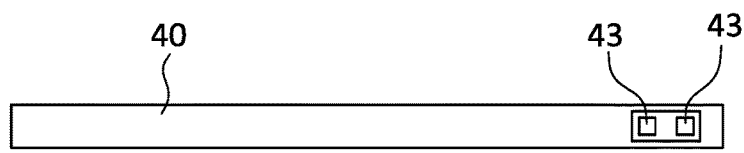
FIG. 11A is a bottom view of the first holder of the embodiment of FIG. 1A.
Figure 11B:
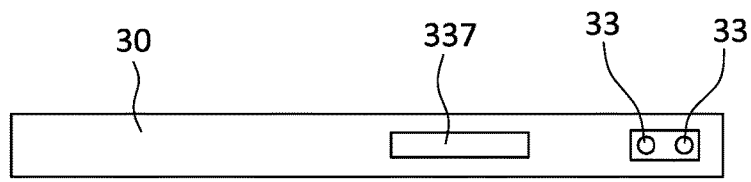
FIG. 11B is a bottom view of the second holder of the embodiment of FIG. 1A.

Referring to FIG. 10, the base 12 is a housing holding electrical components required for charging the digital radiography panel 42 and the computer 50. More specifically, the base 12 includes an AC adapter 220 for the computer 50 and a battery charger 200 (field charge kit) for the digital radiography panel 42 and an AC adapter 210 for the battery charger 200. Instead of separate power supplies for each of the digital radiography panel 42 and the computer 50, a single DC power supply could be used. The output of the battery charger 200 is connected a contact pad 212 including contacts 213, 213 and the output of the AC adapter 220 is connected to a contact pad 222 with contacts 223, 223. FIGS. 11A and 11B show that the bottom of the first holder 40 and the second holder 30 include contacts 33, 33 and 43, 43. These contacts 33, 33 and 43, 43 coincide with contacts 213, 213 and 223, 223, respectively, so that the computer 50 and the digital radiography panel 42 can be charged simultaneously while they are accommodated in the frame 10. To facilitate charging, the base 12 also includes an external connection 240 for receiving a power cable plugged into an outlet. The external connection 240 is connected to each of the power supplies in the base 12 though a power strip 230.

Figure 1B:
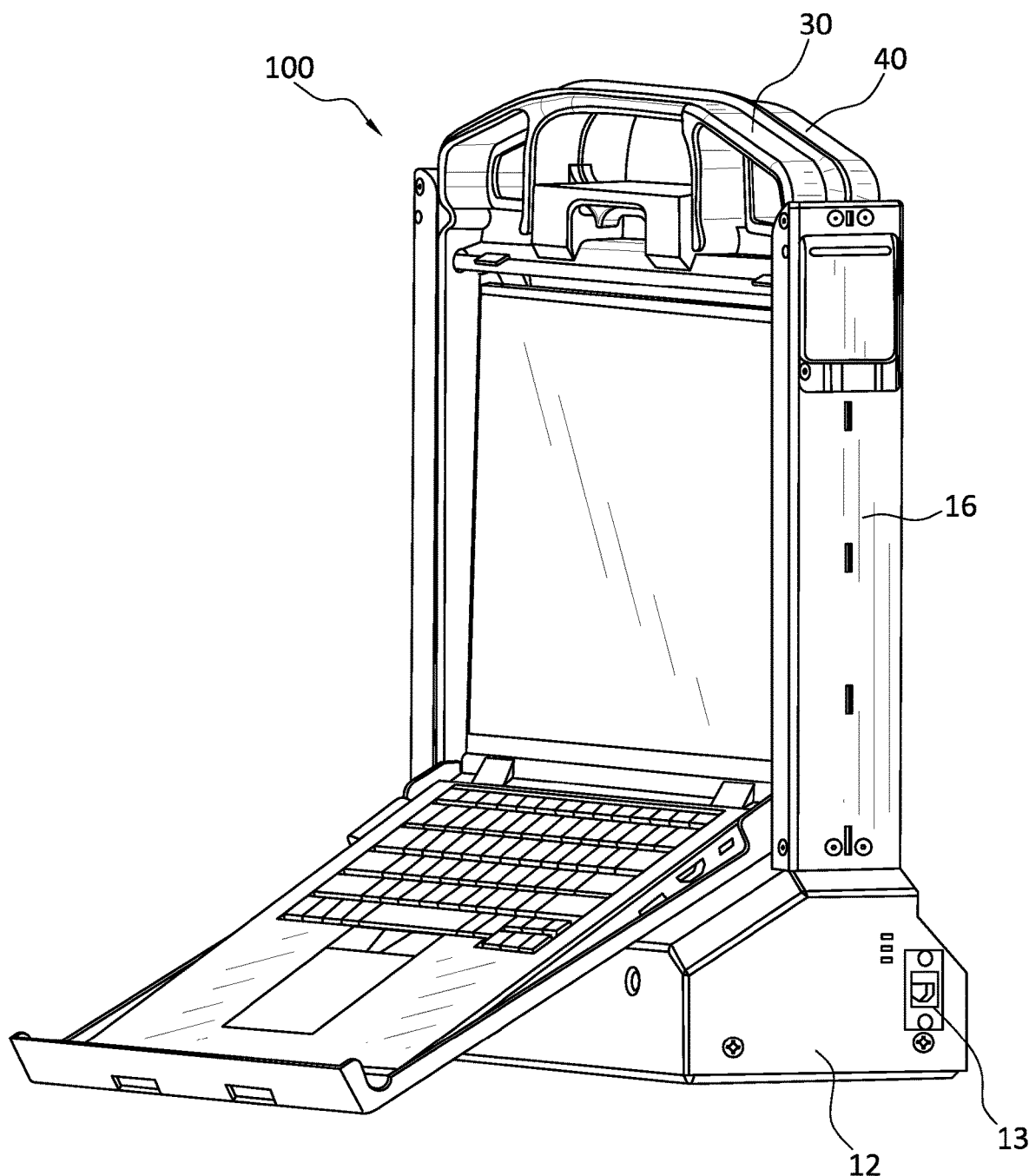
FIG. 1B is a perspective view of the front and right side of the apparatus according to FIG. 1A.

As shown in FIGS. 1B and 10, the base 12 also has an RJ-45 jack 13 that is used to connect to the field charge kit, i.e., the battery charger 200 for the digital radiography panel 42, for servicing.

As is known, the digital radiography panel 42 is capable of wirelessly communicating with the computer 50 through an access point 236 to download images from the digital radiography panel 42 and store the images during imaging of a subject. The access point 236 is powered by a power bank 234, which is in turn charged by a charger 232 connected to the power strip 230. As shown in FIG. 10, the access point 236, the power bank 234, and charger 232 can also be accommodated in the base 12. The access point 236 is connected to a plug 237 that connects with a receptacle 337 on the second holder 30 for signal communication with the computer 50. Instead of using the plug 237, the access point 236 may communicate with the computer 50 wirelessly.

As further shown in FIGS. 10 and 10, the access point 236 may be turned on/off using a power button 15 when not in use. Additional power buttons may be included for the battery charger 200 and the AC adapter 220, for example. Alternatively, a power button may be used to turn on/off all of the electronics in the base 12. A light 16 is used to indicate the state of charge of the power bank 234, another light 17 is used to indicate that the digital radiography panel 42 is charging, and a further light 17A is used to indicate a connection to AC power. Other indicators may be added to indicate charging the computer 50 and the digital radiography panel 42, for example.

Figure 16A:
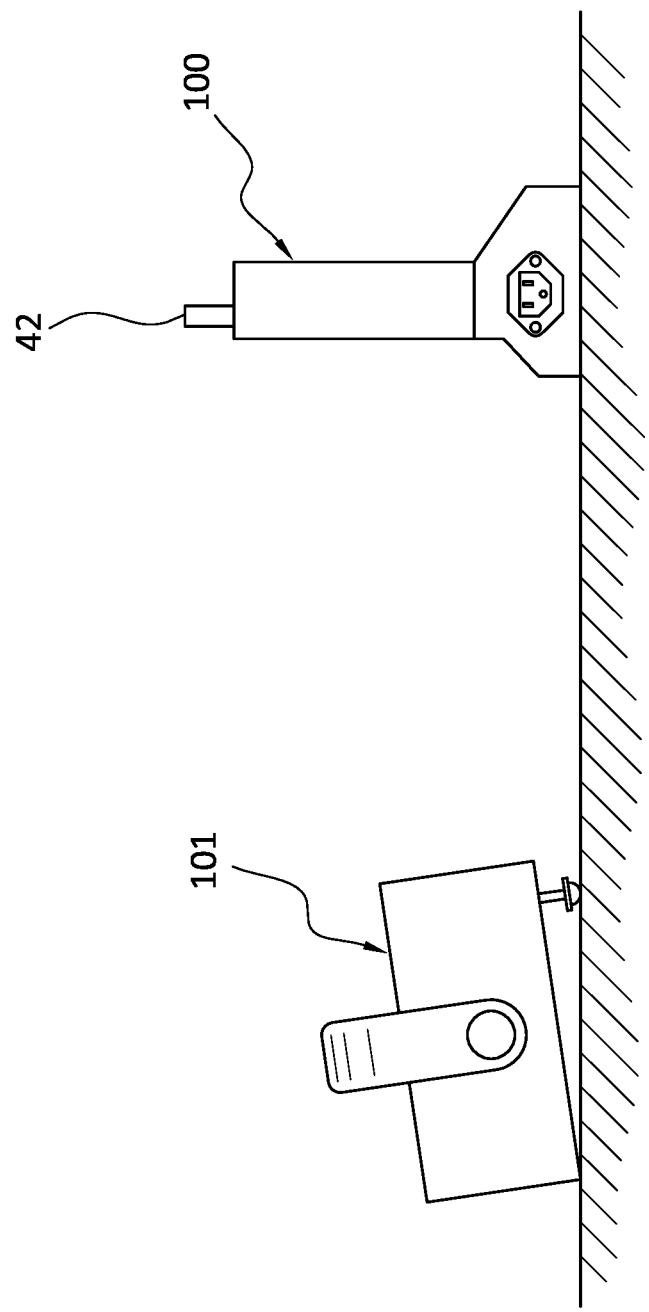
FIG. 16A is a side view of the apparatus of FIG. 1A with an X-ray generator.
Figure 16B:
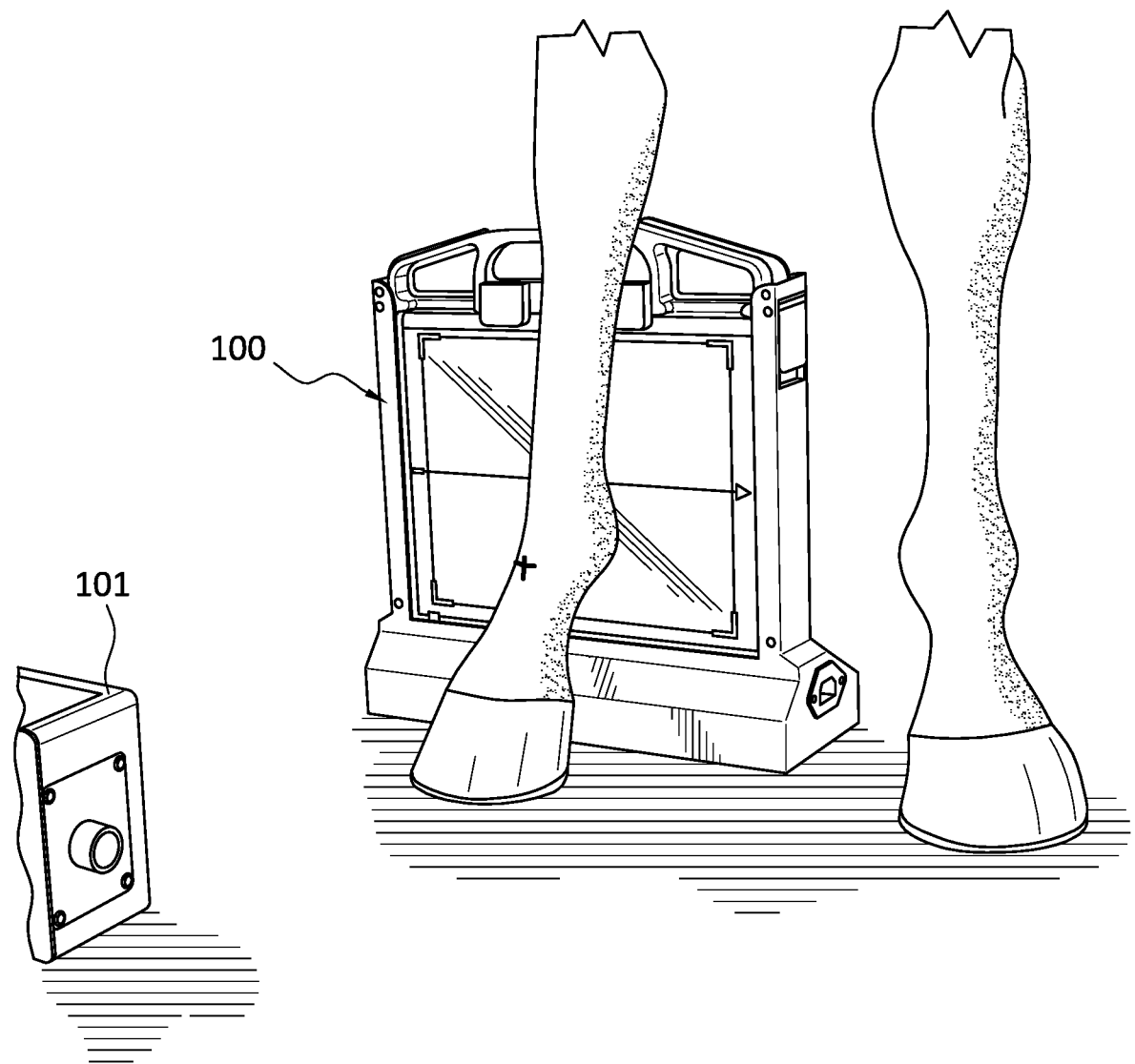
FIG. 16B is a perspective view of the apparatus of FIG. 1A and an X-ray generator positioned to image a leg of an equine subject.
Figure 16C:
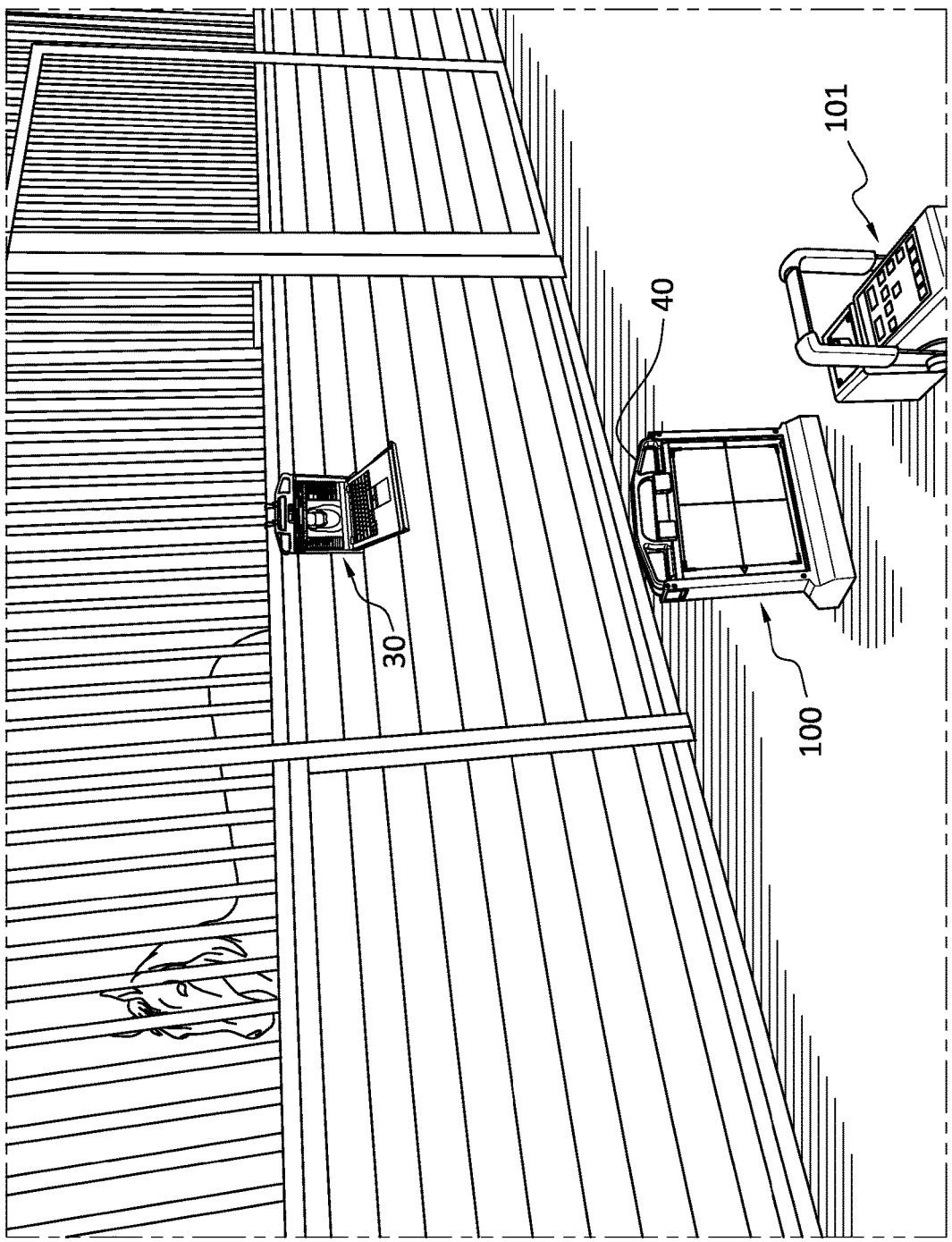
FIG. 16C is a perspective view of the apparatus and an X-ray generator with the second holder hanging on a wall for access by a user.

As shown in FIGS. 16A and 16B, apparatus 100 can be used to hold the panel 42 for imaging. That is, when the first holder 40 with the panel 42 is received in the apparatus, the frame 10 can be used as a stand to hold the panel 42 in a specific position during imaging. This allows the radiographic images to be obtained by a single person when help is not available. In a preferred embodiment, the panel is held by the apparatus in a vertical position. However, the apparatus 100 can be designed to hold the panel in any required position (i.e., a tilted position as described below). As is known, the digital radiography panel 42 is used in conjunction with an X-ray generator 101 to capture images of a subject (see FIGS. 16A, 16B, 16C). Images captured by the panel 42 are uploaded to the computer for viewing using the access point 236. The computer 50 runs a program enabling the computer 50 to communicate with the digital radiography panel 42, download images from the digital radiography panel 42, and present the images on a display for viewing. FIG. 16C shows that the second holder 30 with the computer 50 can be suspended from a hanger or any other support for viewing of images while the panel 42 and X-ray generator 101 are positioned for imaging.

Figure 9:
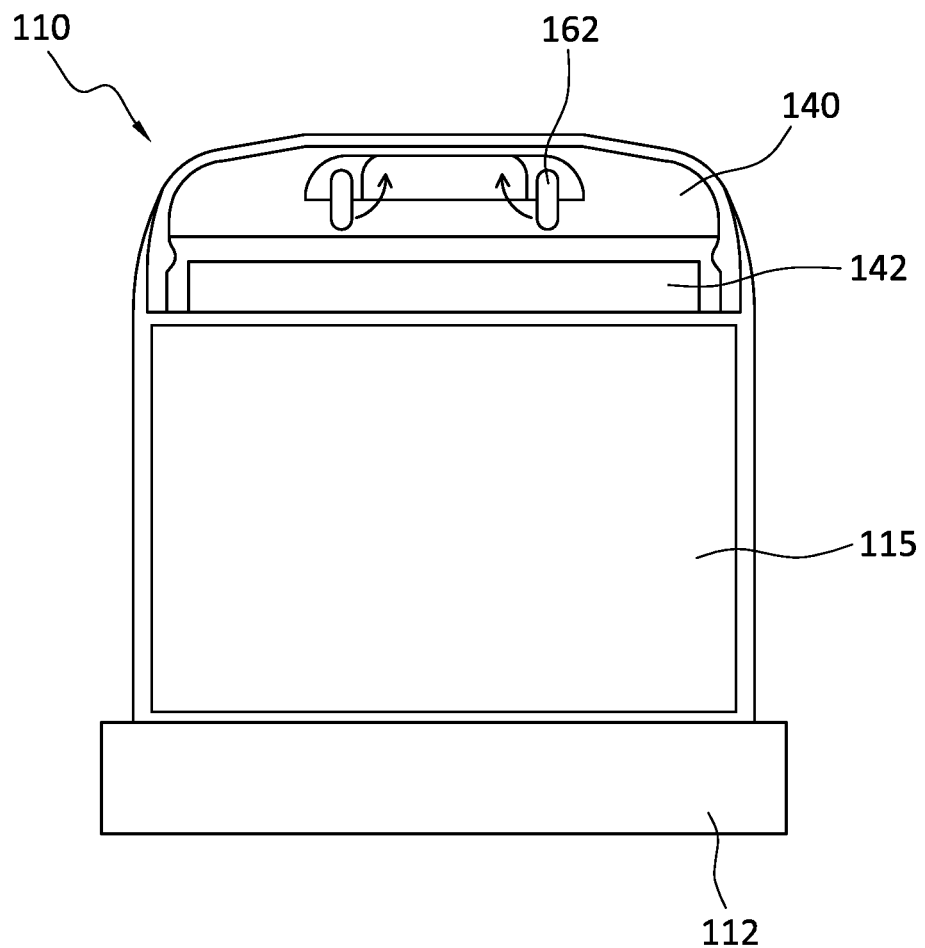
FIG. 9 is a front view of the portable digital radiography apparatus of FIG. 7.

FIGS. 7-9 show a portable digital radiography apparatus 110 according to a further embodiment of the present invention. According to this embodiment, the computer 150 is housed in the apparatus 110 and a holder 140 with the digital radiography panel is inserted into a slot 145 in the apparatus 110. The holder 140 can be locked in place by tabs 162 of a locking mechanism 160. As show in FIG. 9, the tabs 162 can be rotated to provide clearance for the holder 140. After the tabs 162 are rotated, the entire locking mechanism 160 can be pushed rearward to a position shown in FIG. 8, which allows the holder 140 to be lifted out of the apparatus 110. The rearward extending portion of the locking mechanism 160 may be used as a hook so that the apparatus 110 can be hung from a ledge, wall, or any other support during use.

Figure 9A:
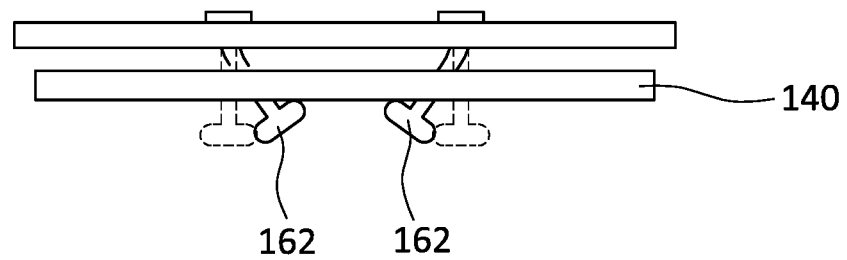
FIG. 9A is a top view of another embodiment of the portable digital radiography apparatus.

FIG. 9A shows a different embodiment of the locking mechanism 160 in which the tabs 162 and locking mechanism are resiliently bent toward each other to release the holder 40. In FIG. 9A, the locking mechanism 160 shown in the unlocked position in solid lines and in the locked position in dashed lines.

The apparatus 110 has a hinged cover 114 on a front side that is movable from a closed position shown in FIG. 9 to an open position shown in FIG. 8. The cover 114 is opened to provide access to the computer 150 (or tablet) mounted therein. In this embodiment, the computer 150 does not have a separate holder, but is mounted directly into the apparatus 110.

The apparatus 110 of FIGS. 7-9 has a base 112 that houses equipment similar to the equipment shown in FIG. 10. However, since the computer 150 does not have a separate holder, contacts are not needed and the computer 150 can be connected to a power source using the conventional plug and socket. The holder 140 has a similar configuration as the holder 40 and has contacts that coincide with contacts in the bottom of slot 145 when the holder is received in the slot 145. Accordingly, the computer 150 and the digital radiography panel 142 held by the holder 140 can be charged simultaneously by the apparatus 110.

Figure 15:
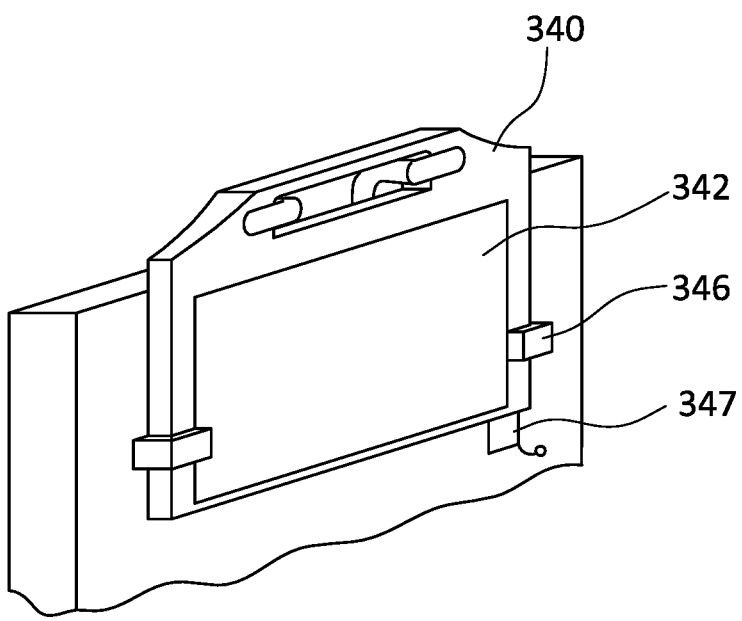
FIG. 15 is a perspective view of the portable radiography apparatus of FIG. 12A with a clamp for holding the panel onto the frame.

FIGS. 12A-14 show a portable digital radiography apparatus 310 according to a further embodiment of the present invention. The apparatus 310 includes a base 312 and a frame 314 pivotally mounted on the base 312. According to this embodiment, a tablet 350 is mounted on one side of the frame 314 and a holder 340 holding a digital radiography panel 342 is mounted on the opposite side of the frame 314. The bottom of the holder 340 is received in a receptacle 345 on the frame 314. Instead of the receptacle, the holder 340 and the panel 342 may be held against the frame 314 by clamps 346 as shown in FIG. 15.

Figure 12A:
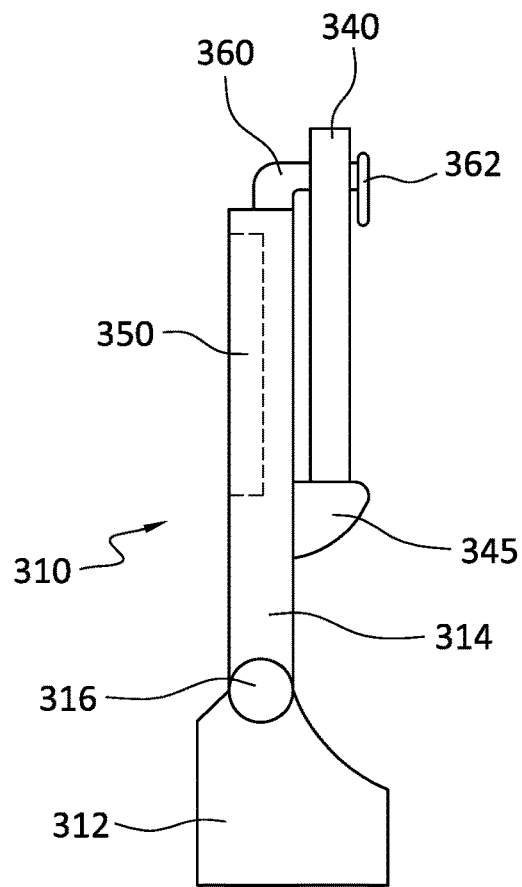
FIG. 12A is a side view of a portable digital radiography apparatus according to a third embodiment of the present invention with a holder of a digital radiography panel mounted thereon.
Figure 12B:
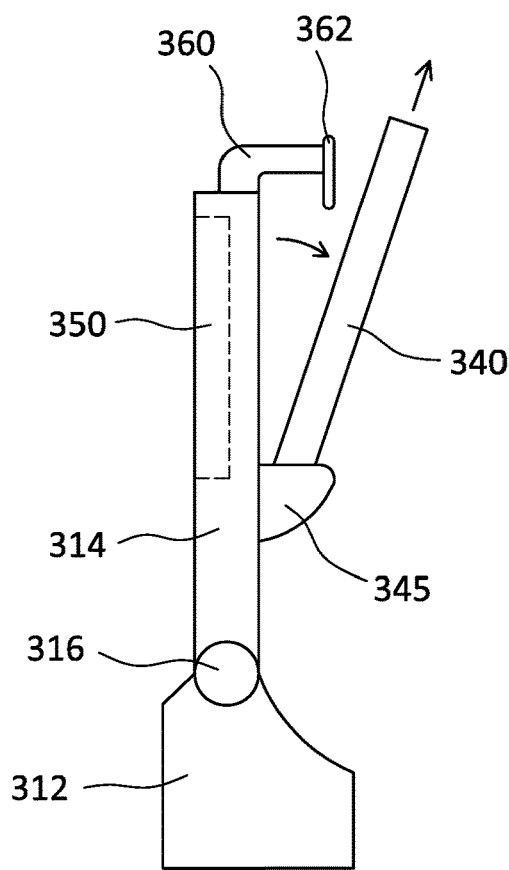
FIG. 12B is a side view of the portable digital radiography apparatus of FIG. 12A showing a position of the holder of the digital radiography panel tilted away from the apparatus.

The portable digital radiography apparatus 310 includes a locking mechanism 360 with tabs 362 for locking the holder 340 on the frame 314. When the tabs 362 have locked the holder 340 in place, the entire portable digital radiography apparatus 310 can be lifted by the handle of the holder 340. The tabs 362 are rotatable to an unlocked position to provide clearance for and unlock the holder 340. After the tabs 362 are rotated to the unlocked position, the holder 340 can be tilted away from the frame 314 and then lifted out of the receptacle 345 as shown in FIG. 12B.

Figure 13:
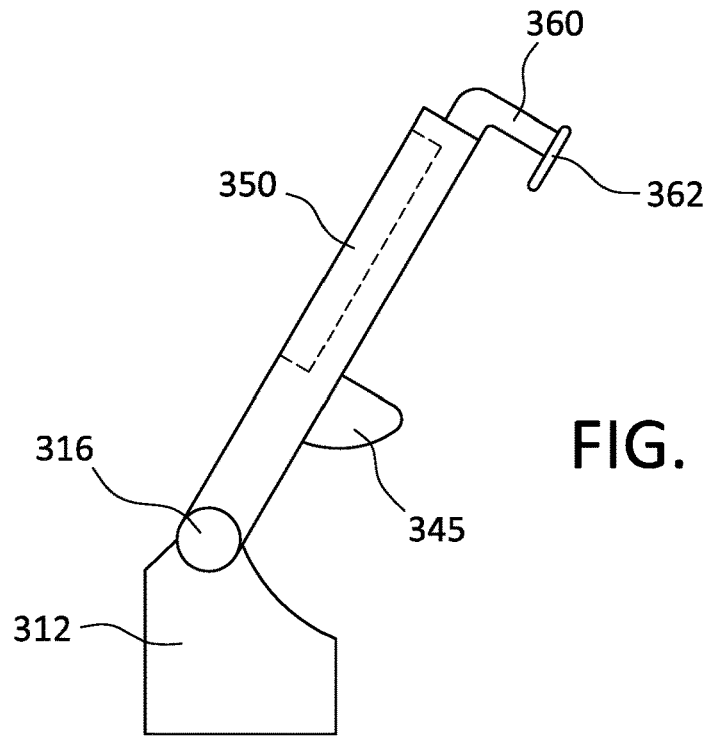
FIG. 13 is a side view of the portable digital radiography apparatus of FIG. 12A in a tilted configuration.
Figure 14:
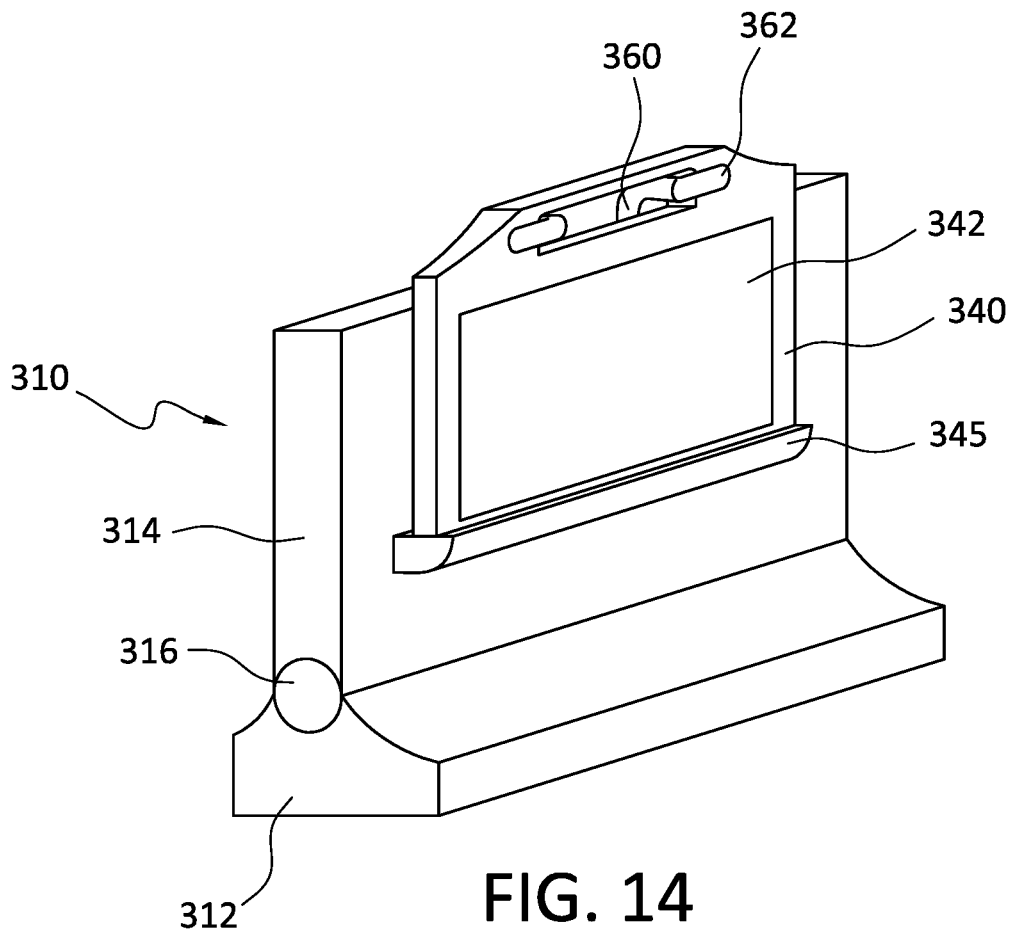
FIG. 14 is a perspective view of a front and side of the portable digital radiography apparatus of FIG. 12A.

As shown in FIG. 13, the frame 314 can be tilted or pivoted about an axis 316 relative to the base 312. The pivoting is used to afford a better viewing angle for the display of the tablet 350. Alternatively, or additionally, the frame 314 can be tilted to hold the panel 342 at an angle required for imaging. For example, the apparatus 310 can be used as an adjustable stand for the panel.

The apparatus 310 of FIGS. 12A-14 has a base 312 that houses equipment similar to the equipment shown in FIG. 10. However, since the tablet 350 does not have a separate holder, contacts are not needed and the tablet 350 can be connected to a power source using the conventional plug and socket. The holder 340 has a similar configuration as the holder 40 and has contacts that coincide with contacts in the bottom of receptacle 345 when the holder 340 is received in the receptacle 345. Accordingly, the tablet and the digital radiography panel held by the holder 340 can be charged simultaneously. In the embodiment of FIG. 15, a plug 347 may be used to establish an electrical connection to the charger. In this case, the plug 347 must be manually connected to the holder 340/panel 342.

Figure 17:
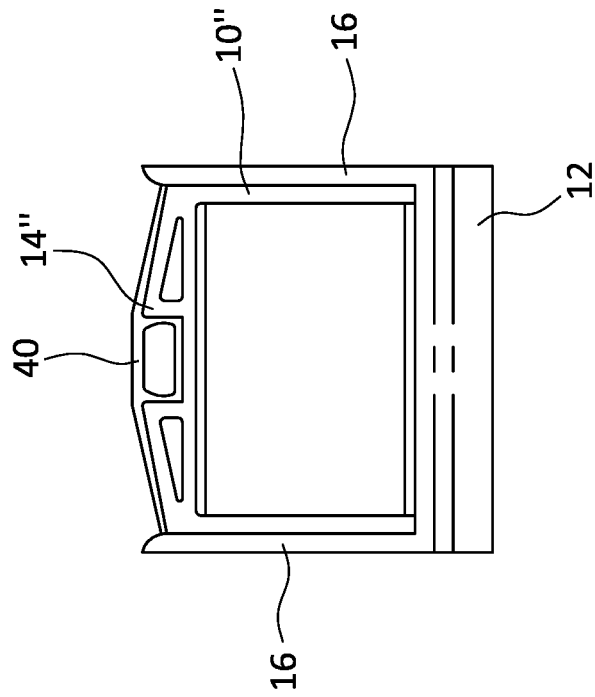
FIG. 17 is a front view of a frame according to another embodiment of the present invention.
Figure 18:
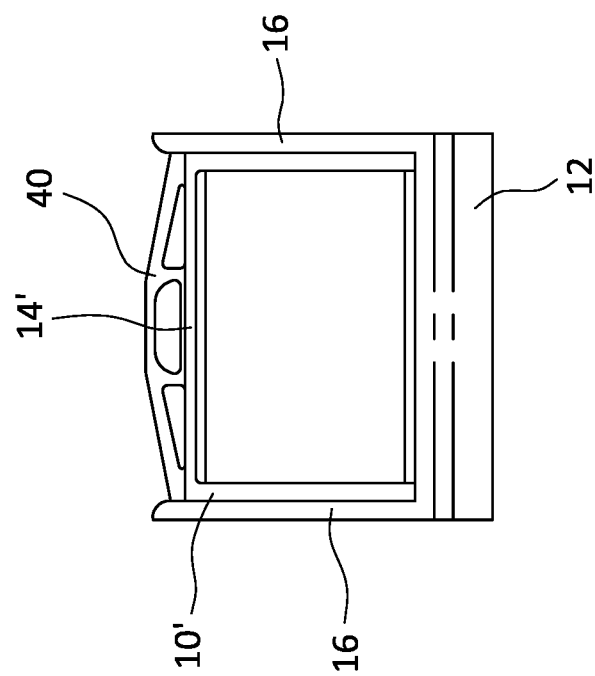
FIG. 18 is a front view of a frame according to yet another embodiment of the present invention.
Figure 22:
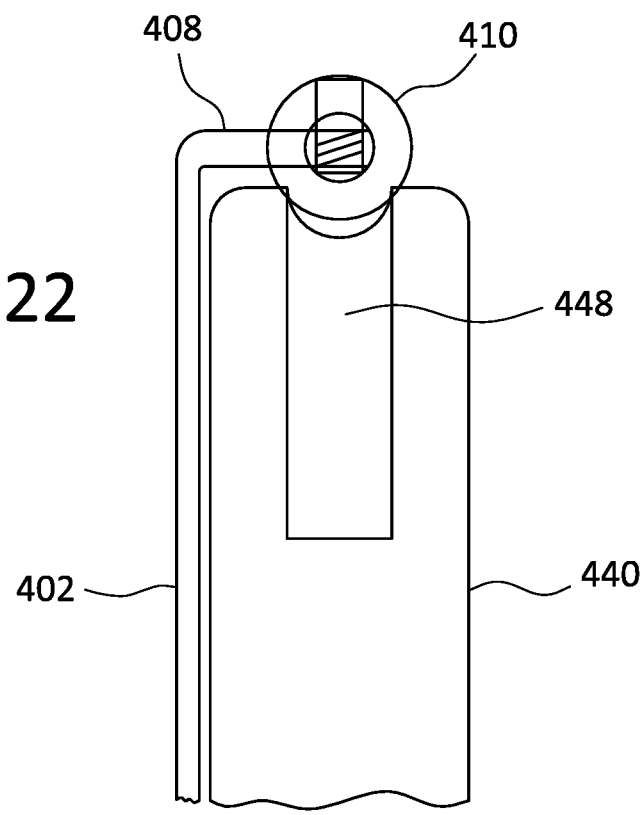
FIG. 22 is a side view of a top of the bracket of FIG. 20 with a holder.
Figure 23:
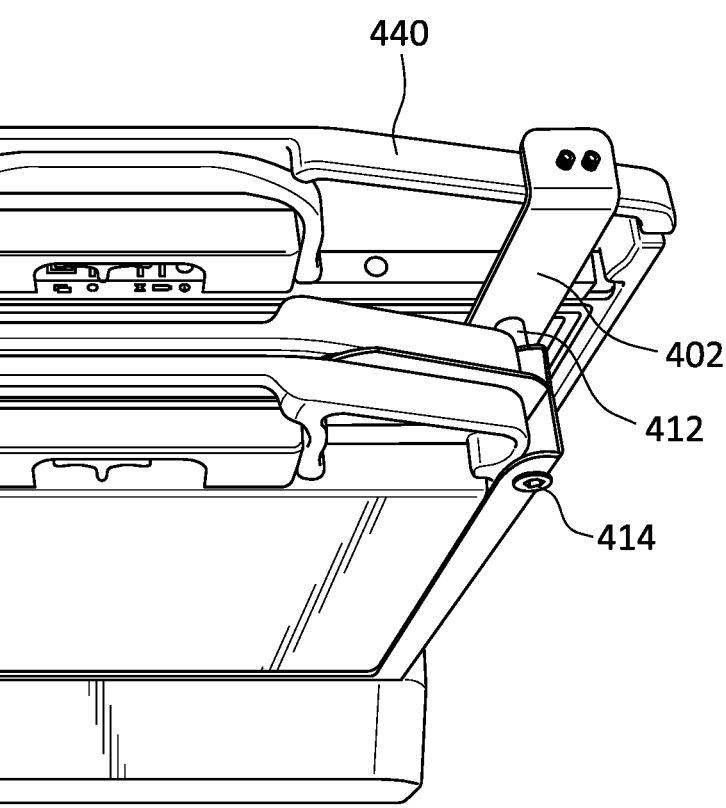
FIG. 23 is a top view of the embodiment of FIG. 19.

As described above, the handle 14 of the frame 10 may be replaced with a frame 10' having a bar 14' (FIG. 17) or a frame 10" having an other shaped structure 14" (FIG. 18) between the side rails 16. FIGS. 17 and 18 each show the first holder 40 accommodated in the apparatus with the handle portion 41 in relation to the bar 14' and other shaped structure 14". The omission of the handle 14 from the embodiments of FIGS. 17 and 18 prevents pinching of a user's hand between the holders 30, 40 and the frame 10 when grasping the handle portions 31, 41. In the embodiments of FIGS. 17 and 18, the apparatus 100 is picked up by the handle portions 41, 31 of the first holder 40 and second holder 30 via the locking levers 18.

Figure 1C:
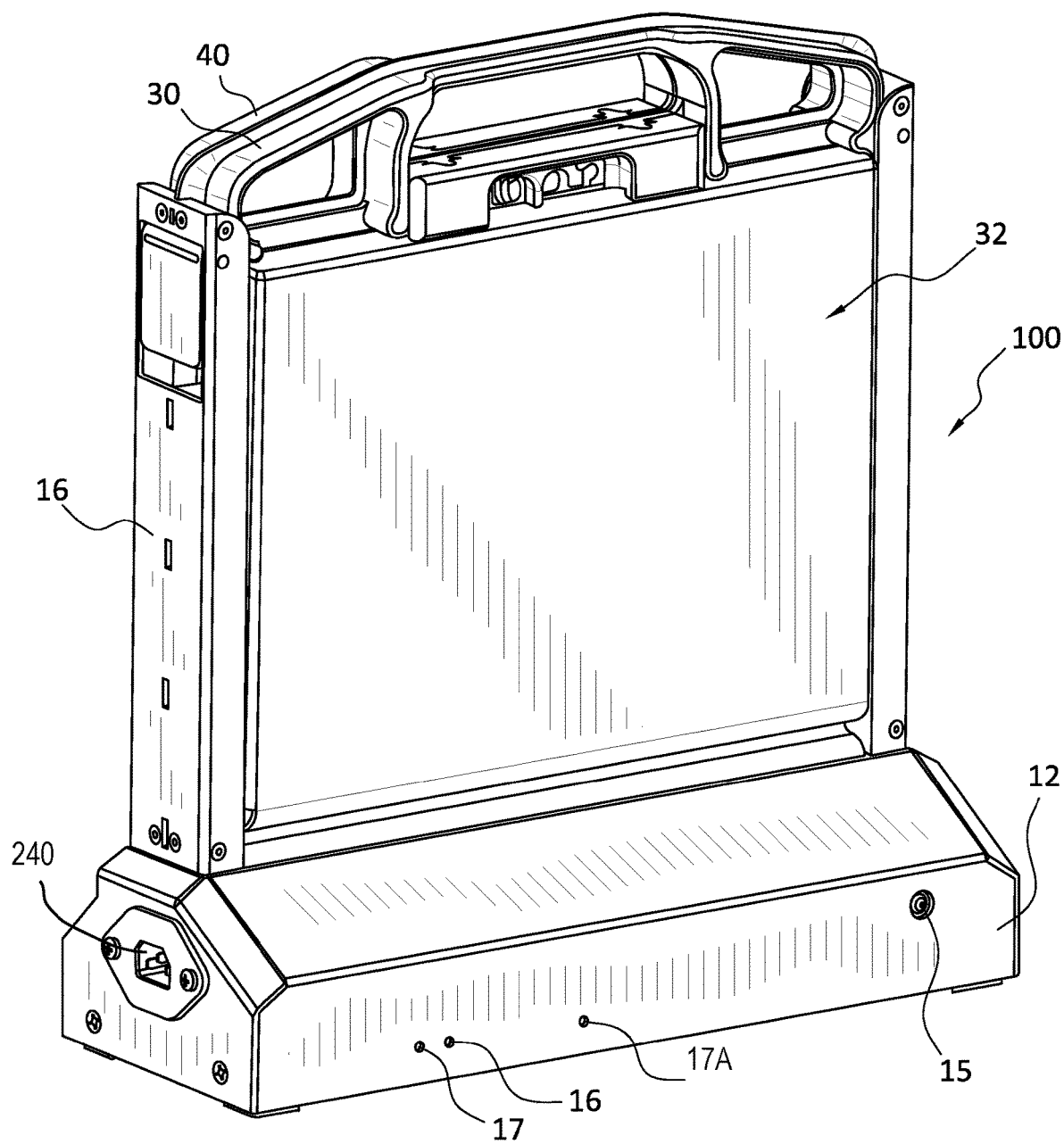
FIG. 1C is the same view of the apparatus in FIG. 1A in which a second holder for a computer is in a closed position.

In yet another embodiment of the invention shown in FIGS. 19-23, an additional mounting 400 may be added to the apparatus 100 of FIGS. 1A-1C. Although the additional mounting 400 is shown on apparatus 100, the additional mounting 400 could also be incorporated in any other embodiments of the present invention such as the apparatus 110 and 310. The additional mounting 400 includes a pair of brackets 402, 402 attached to the frame 10. The brackets 402, do accommodate a third holder 440, which holds an additional digital radiography panel 442. In the embodiment of FIGS. 19-23, the additional digital radiography panel 442 is larger than the digital radiography panel 42. More specifically, the digital radiography panel 42 is a 10"×12" panel and the additional digital radiography panel 442 is a 14"×17" panel. Although the panels are shown as having two different sizes, they may also be the same size, or the additional digital radiography panel 442 may be smaller than the digital radiography panel 42.

Each of the brackets 402 is a flat stock bar with a back section 403, a horizontal bottom section 404, vertical front section 406 extending upward from the horizontal bottom section 404, and a horizontal top section 408. The back section 403 extends an entire length of the additional mounting 400. The bottom of the third holder 440 is received by the brackets 402 in the space defined by the back section 403, the horizontal bottom section 404, and the vertical front section 406. The top of the third holder 440 has a groove 448 in which a spacer or abutment 410 connected to the horizontal top section 408 is received to hold the third holder 440 in place. The third holder 440 is removable by pulling the top of the third holder 440 horizontally away from apparatus 100 until the horizontal top section 408 is cleared and then lifting the third holder out of the brackets 402, 402.

Each bracket 402 is attached to the apparatus 100 by a threaded fastener 414. The threaded fastener 414 passes through the frame 10 and serves as the pivot axis for the locking levers 18. As an alternative, the threaded fastener 414 could be attached to any part of the frame 10. The bottom of back section 403 of the bracket 402 abuts the base 12. In one embodiment, the back section 403 of the bracket 402 is connected to the base 12 by a double-sided tape or an adhesive. Although a double-sided tape or an adhesive is preferred, the back section 403 of the bracket 402 can be connected to the base or any other part of the apparatus 100 using any other connecting means such as, for example, a threaded fastener or a rivet. The horizontal bottom section 404 of the bracket 402 is preferably flush with the bottom of the base 12, which added stability to the apparatus 100. In other embodiments, the horizontal bottom section 404 could be disposed above the bottom of the base 12.

A spacer 412 is disposed on the fastener 414 so that the back section 3 of the bracket 402 is held vertically on the apparatus 100. The spacer 412 is depicted as a tube that surrounds the threaded fastener 414. However, the spacer 412 could be located anywhere between the bracket 402 and the frame 10. For example, the spacer 412 could be a block of rubber, plastic, or any other material arranged between the bracket 402 and the frame 10, and connected to the bracket 402 and/or the frame 10 by an adhesive or any other connecting method.

The embodiment of FIGS. 19-23 further includes a support 450 having a leg 451 that pivotable between a stowed position (FIG. 19) and a deployed position (FIG. 21). The support 450 is arranged on a side of the apparatus 100 opposite from the brackets 402. When the leg 451 is deployed, the apparatus 100 can be laid on its side with the third holder facing upward and being parallel with the ground as shown in FIG. 21. In this position, the subject on which radiography is performed can be placed over the digital radiography panel 442. The support 450 can be centrally between the two side rails 16 of the frame 10.

Alternatively, a pair of supports 450 can be used respectively mounted on the two side rails 16 for a more stable arrangement.

While the preferred embodiments are described above, the invention is not limited to these specific embodiments. Features of one embodiment may be incorporated into other embodiments. For example, the holder 30 for the computer or tablet of the first embodiment of FIG. 1 could be incorporated in the embodiments of FIG. 7-9 or 12A-14. The invention should only be limited by the claims that follow.

What is claimed is:

1. A portable digital radiography apparatus, comprising:
   a frame including a base;
   a radiography panel configured to generate images of a subject when exposed to a radiography source, the frame being configured to support the radiography panel in a position for imaging the subject when the radiography panel is accommodated in the frame;
   a computer configured to download the images from the radiography panel, the frame being configured to accommodate the computer; and
   a charging system disposed in the base, the charging system being connectable to the radiography panel and the computer, and configured to charge both the radiography panel and the computer when the radiography panel and the computer are accommodated on the frame,
   wherein the frame, the radiography panel, the computer, and the charging system are transportable as an integral unit when the radiography panel and the computer are accommodated on the frame.

2. The portable digital radiography apparatus of claim 1, further comprising a first holder in which the radiography panel is mounted, the frame is configured to accommodate the first holder with the radiography panel, the first holder has a first holder handle, and the frame is liftable by the first holder handle when the first holder is accommodated on the frame.

3. The portable digital radiography apparatus of claim 2, further comprising a second holder having an enclosure in which the computer is mounted, the frame is configured to accommodate the second holder with the computer, and the second holder having a second holder handle.

4. The portable digital radiography apparatus of claim 3, wherein the frame further includes side rails defining slots in which side walls of the first holder and side walls of the second holder are slidably received, whereby each of the first holder and the second holder is vertically receivable in the frame and vertically removable from the frame via the slots.

5. The portable digital radiography apparatus of claim 4, further comprising a recess in at least one of the side walls of the first holder, a recess in at least one of the side walls of the second holder, and at least one locking lever, each of the at least one locking lever being arranged on one of the side rails and being movable from a locked position to an unlocked position, the at least one locking lever engages the recess in the at least one of the side walls of the first holder and the recess in the at least one of the side walls of the second holder when the at least one locking lever is in the locked position, and the at least one locking lever allows removal of the first holder and the second holder when the at least one locking lever is in the unlocked position.

6. The portable digital radiography apparatus of claim 5, wherein the frame is liftable by the first holder handle and the second holder handle when the first holder and the second holder are accommodated on the frame and the at least one locking lever is in the locked position.

7. The portable digital radiography apparatus of claim 1, wherein the base includes electrical connection elements for forming an electrical connection between the charging system and both the computer and the radiography panel, wherein both the computer and the radiography panel can be charged simultaneously through the base.

8. The portable digital radiography apparatus of claim 7, further comprising a panel power supply arranged in the base for charging the radiography panel, the frame includes a first set of contacts connected to the panel power supply, and the first holder includes a second set of contacts that coincide with the first set of contacts and provide an electrical connection between the radiography panel and the panel power supply.

9. The portable digital radiography apparatus of claim 7, further including a second holder having an enclosure in which the computer is mounted, the enclosure having a hinged cover that opens to provide an access to the computer, and the frame being configured to accommodate the second holder with the computer.

10. The portable digital radiography apparatus of claim 9, wherein the computer comprises a laptop computer having a keyboard and the hinged cover supports the keyboard.

11. The portable digital radiography apparatus of claim 9, wherein the enclosure is removable from the frame.

12. The portable digital radiography apparatus of claim 11, further comprising a computer power supply for charging the computer arranged in the base, the frame including a third set of contacts connected to the computer power supply, and the second holder includes a fourth set of contacts that coincide with the third set of contacts and provide an electrical connection between the computer and the computer power supply.

13. The portable digital radiography apparatus of claim 1, further comprising a locking element capable of holding the radiography panel onto the frame.

14. The portable digital radiography apparatus of claim 13, further comprising a first holder in which the radiography panel is mounted, wherein the locking element is further capable of holding the computer onto the frame, the frame has a frame handle, and the frame, the computer, and the radiography panel can be carried using the frame handle when the radiography panel and the computer are held onto the frame by the locking element.

15. The portable digital radiography apparatus of claim 1, wherein a part of the frame accommodating the radiography panel is pivotable relative to the base.

16. The portable digital radiography apparatus of claim 1, wherein the radiography panel is configured to capture images while accommodated on the frame, whereby the frame acts as a stand for the radiography panel.

17. The portable digital radiography apparatus of claim 1, further comprising a mounting connected to the frame for accommodating an additional radiography panel.

18. The portable digital radiography apparatus of claim 17, further comprising an additional radiography panel, wherein the mounting supports a bottom and a top of the additional radiography panel.

19. The portable digital radiography apparatus of claim 18, further comprising a support leg that is movable between a stowed position and a deployed position, the support leg supporting the frame when the frame is laid on a side opposite to the mounting so that the additional radiography panel is facing upward and is parallel to the ground.

20. A portable digital radiography apparatus, comprising:
a frame including a base;
a radiography panel configured to generate images of a subject when exposed to a radiography source, the frame being configured to support the radiography panel in a position for imaging a subject when the radiography panel is accommodated on the frame; and
a computer configured to download the images from the radiography panel, the frame being configured to accommodate the computer,
wherein the frame, the radiography panel, and the computer are transportable as an integral unit when the radiography panel and the computer are accommodated on the frame.

21. The portable digital radiography apparatus of claim 20, further comprising a first holder in which the radiography panel is mounted, the frame being configured to accommodate the first holder with the radiography panel, the first holder having a first holder handle, and the frame, the computer, and the radiography panel being liftable together by the first holder handle when the first holder is accommodated on the frame.

22. The portable digital radiography apparatus of claim 21, further comprising a second holder having an enclosure in which the computer is mounted, the frame is configured to accommodate the second holder with the computer, and the second holder having a second holder handle.

23. The portable digital radiography apparatus of claim 22, wherein the frame further includes side rails defining slots in which side walls of the first holder and side walls of the second holder are slidably received, whereby each of the first holder and the second holder is vertically receivable in the frame and vertically removable from the frame via the slots.

24. The portable digital radiography apparatus of claim 23, further comprising a recess in at least one of the side walls of the first holder, a recess in at least one of the side walls of the second holder, and at least one locking lever, each of the at least one locking lever being arranged on one of the side rails and being movable from a locked position to an unlocked position, the at least one locking lever engages the recess in the at least one of the side walls of the first holder and the recess in the at least one of the side walls of the second holder when the at least one locking lever is in the locked position, and the at least one locking lever allows removal of the first holder and the second holder when the at least one locking lever is in the unlocked position.

25. The portable digital radiography apparatus of claim 20, further comprising a second holder having an enclosure in which the computer is mounted, the frame being configured to accommodate the second holder with the computer, the second holder having a second holder handle, and the frame, the computer, and the radiography panel being liftable together by the second holder handle when the second holder is accommodated on the frame.

* * * * *